(12) United States Patent
Poll et al.

(10) Patent No.: US 9,078,562 B2
(45) Date of Patent: Jul. 14, 2015

(54) SYSTEMS AND METHODS FOR OPTIMIZING AND MAINTAINING VISUALIZATION OF A SURGICAL FIELD DURING THE USE OF SURGICAL SCOPES

(75) Inventors: Wayne L. Poll, New Albany, OH (US); Caroline M. Crisafulli, Columbus, OH (US); Gregory P. Drach, Liberty Township, OH (US)

(73) Assignee: Minimally Invasive Devices, Inc., Columbus, OH (US)

( * ) Notice: Subject to any disclaimer, the term of this patent is extended or adjusted under 35 U.S.C. 154(b) by 98 days.

(21) Appl. No.: 13/166,502

(22) Filed: Jun. 22, 2011

(65) Prior Publication Data
US 2012/0165610 A1 Jun. 28, 2012

Related U.S. Application Data

(63) Continuation-in-part of application No. 13/004,505, filed on Jan. 11, 2011.

(60) Provisional application No. 61/335,712, filed on Jan. 11, 2010.

(51) Int. Cl.
*A61B 1/12* (2006.01)
*A61M 1/00* (2006.01)
(Continued)

(52) U.S. Cl.
CPC ............ *A61B 1/015* (2013.01); *A61B 1/00119* (2013.01); *A61B 1/313* (2013.01);
(Continued)

(58) Field of Classification Search
CPC .......................... A61M 13/003; A61M 13/006
USPC .................. 600/156–158; 604/23, 26, 27, 35, 604/43–45, 540
See application file for complete search history.

(56) References Cited

U.S. PATENT DOCUMENTS

| 3,373,736 A | 3/1968 | Fiore et al. |
| D230,727 S | 3/1974 | Richman |

(Continued)

FOREIGN PATENT DOCUMENTS

| EP | 0664101 A1 | 7/1995 |
| EP | 1188415 A2 | 3/2002 |

(Continued)

OTHER PUBLICATIONS

Farley et al.; Double-blind, prospective, randomized study of warmed, humidified carbon dioxide insufflation vs standard carbon dioxide for patients undergoing lararoscopic cholecystectomy; Arch Surg; 139; pp. 739-744; Jul. 2004.

(Continued)

*Primary Examiner* — Anhtuan T Nguyen
*Assistant Examiner* — Aaron B Fairchild
(74) *Attorney, Agent, or Firm* — Shay Glenn LLP

(57) ABSTRACT

Systems and methods condition air for passage across a laparoscopic lens to prevent fogging, deflect debris, and maintain visualization of an operating cavity. The systems and methods provide an access device sized and configured to provide communication with an insufflated CO2 environment maintained by operation of an insufflations circuit. The access device is coupled to an air conditioning set, which interacts with an air conditioning driver to condition air from the insufflated environment for continuous passage across the laparoscopic lens, to thereby maintain visualization by the laparoscopic lens of the operating cavity, independent of operation of the insufflator circuit.

14 Claims, 30 Drawing Sheets

(51) Int. Cl.

| | | |
|---|---|---|
| *A61M 37/00* | (2006.01) | |
| *A61B 1/015* | (2006.01) | |
| *A61B 1/00* | (2006.01) | |
| *A61B 1/313* | (2006.01) | |
| *A61B 1/32* | (2006.01) | |
| *A61B 17/34* | (2006.01) | |
| *A61M 13/00* | (2006.01) | |
| *A61B 19/00* | (2006.01) | |
| *A61B 17/00* | (2006.01) | |

(52) U.S. Cl.
CPC .............. *A61B 1/32* (2013.01); *A61B 17/3421* (2013.01); *A61M 13/006* (2014.02); *A61B 17/3474* (2013.01); *A61B 19/34* (2013.01); *A61B 2017/00296* (2013.01); *A61B 2017/3454* (2013.01); *A61B 2218/006* (2013.01); *A61B 2218/008* (2013.01); *A61M 13/003* (2013.01)

(56) References Cited

U.S. PATENT DOCUMENTS

| | | | |
|---|---|---|---|
| 4,207,874 A | 6/1980 | Choy | |
| 4,279,246 A | 7/1981 | Chikama | |
| 4,281,646 A | 8/1981 | Kinoshita | |
| D277,408 S | 1/1985 | Kubokawa et al. | |
| D277,505 S | 2/1985 | Kubokawa et al. | |
| 4,497,550 A | 2/1985 | Ouchi et al. | |
| 4,537,209 A | 8/1985 | Sasa | |
| D280,929 S | 10/1985 | Lystager | |
| 4,548,197 A | 10/1985 | Kinoshita | |
| 4,552,130 A | 11/1985 | Kinoshita | |
| D284,028 S | 5/1986 | Seager | |
| 4,598,698 A | 7/1986 | Siegmund | |
| 4,616,169 A * | 10/1986 | Proffitt | 320/111 |
| 4,617,013 A | 10/1986 | Betz | |
| 4,633,855 A | 1/1987 | Baba | |
| 4,637,814 A | 1/1987 | Leiboff | |
| 4,646,722 A | 3/1987 | Silverstein et al. | |
| 4,735,603 A * | 4/1988 | Goodson et al. | 604/21 |
| 4,741,326 A | 5/1988 | Sidall et al. | |
| 4,748,970 A | 6/1988 | Nakajima | |
| 4,760,838 A | 8/1988 | Fukuda | |
| 4,773,413 A | 9/1988 | Hussein et al. | |
| 4,794,911 A | 1/1989 | Okada | |
| 4,800,869 A | 1/1989 | Nakajima | |
| 4,877,016 A | 10/1989 | Kantor et al. | |
| 4,941,872 A | 7/1990 | Felix et al. | |
| 4,973,321 A | 11/1990 | Michelson | |
| 4,991,565 A | 2/1991 | Takahashi et al. | |
| 4,998,527 A | 3/1991 | Meyer | |
| 5,009,655 A | 4/1991 | Daignault, Jr. et al. | |
| 5,019,054 A | 5/1991 | Clement et al. | |
| 5,027,791 A | 7/1991 | Takahashi | |
| 5,050,585 A | 9/1991 | Takahashi | |
| 5,133,336 A | 7/1992 | Savitt et al. | |
| 5,144,942 A | 9/1992 | Decarie et al. | |
| 5,147,292 A | 9/1992 | Kullas et al. | |
| 5,163,927 A | 11/1992 | Woker et al. | |
| 5,167,220 A | 12/1992 | Brown | |
| 5,201,908 A | 4/1993 | Jones | |
| 5,207,213 A | 5/1993 | Auhll et al. | |
| 5,225,001 A | 7/1993 | Manni et al. | |
| 5,279,549 A | 1/1994 | Ranford | |
| D346,023 S | 4/1994 | Stewart, Sr. | |
| 5,306,272 A | 4/1994 | Cohen et al. | |
| 5,312,400 A | 5/1994 | Bales et al. | |
| 5,313,934 A | 5/1994 | Wiita et al. | |
| 5,320,091 A | 6/1994 | Grossi et al. | |
| 5,328,458 A | 7/1994 | Sekino et al. | |
| 5,336,170 A | 8/1994 | Salerno et al. | |
| 5,339,800 A | 8/1994 | Wiita et al. | |
| 5,359,991 A | 11/1994 | Takahashi et al. | |
| 5,364,407 A | 11/1994 | Poll | |
| 5,386,817 A | 2/1995 | Jones | |
| 5,392,766 A | 2/1995 | Masterson et al. | |
| 5,400,767 A | 3/1995 | Murdoch | |
| 5,448,891 A | 9/1995 | Nakagiri et al. | |
| 5,448,990 A | 9/1995 | De Faria Correa | |
| 5,464,008 A | 11/1995 | Kim | |
| 5,468,240 A | 11/1995 | Gentelia et al. | |
| D369,862 S | 5/1996 | Stewart, Jr. | |
| 5,514,084 A | 5/1996 | Fisher | |
| 5,518,502 A | 5/1996 | Kaplan et al. | |
| 5,562,600 A | 10/1996 | Matsuno | |
| 5,563,737 A | 10/1996 | Kamrat | |
| 5,569,157 A | 10/1996 | Nakazawa et al. | |
| 5,575,753 A | 11/1996 | Yabe et al. | |
| 5,575,756 A | 11/1996 | Karasawa et al. | |
| 5,605,532 A | 2/1997 | Schermerhorn | |
| 5,630,795 A | 5/1997 | Kuramoto et al. | |
| 5,637,075 A | 6/1997 | Kikawada | |
| 5,647,840 A | 7/1997 | D'Amelio et al. | |
| 5,697,888 A | 12/1997 | Kobayashi et al. | |
| 5,746,695 A | 5/1998 | Yasui et al. | |
| 5,788,628 A | 8/1998 | Matsuno et al. | |
| 5,865,730 A | 2/1999 | Fox et al. | |
| 5,868,663 A | 2/1999 | Katsurada et al. | |
| 5,869,107 A | 2/1999 | Shimizu et al. | |
| 5,894,369 A | 4/1999 | Akiba et al. | |
| 5,922,105 A | 7/1999 | Fujii et al. | |
| 5,954,637 A | 9/1999 | Francis | |
| 5,957,888 A | 9/1999 | Hinchliffe | |
| 5,989,183 A | 11/1999 | Reisdorf et al. | |
| 6,017,333 A | 1/2000 | Bailey | |
| 6,040,053 A | 3/2000 | Scholz et al. | |
| 6,071,606 A | 6/2000 | Yamazaki et al. | |
| D428,487 S | 7/2000 | Renner et al. | |
| 6,096,026 A | 8/2000 | Schultz | |
| 6,110,103 A | 8/2000 | Donofrio | |
| 6,110,259 A | 8/2000 | Schultz et al. | |
| 6,126,592 A | 10/2000 | Proch et al. | |
| 6,149,659 A | 11/2000 | Ahmed | |
| 6,156,409 A | 12/2000 | Doushita et al. | |
| 6,176,825 B1 | 1/2001 | Chin et al. | |
| 6,234,635 B1 | 5/2001 | Seitzinger et al. | |
| 6,282,442 B1 | 8/2001 | DeStefano et al. | |
| 6,299,592 B1 | 10/2001 | Zander | |
| 6,306,932 B1 | 10/2001 | Yamamoto et al. | |
| 6,354,992 B1 | 3/2002 | Kato | |
| 6,361,492 B1 | 3/2002 | Santilli | |
| 6,383,134 B1 | 5/2002 | Santilli | |
| 6,409,657 B1 | 6/2002 | Kawano | |
| 6,425,535 B1 | 7/2002 | Akiba | |
| 6,447,446 B1 | 9/2002 | Smith et al. | |
| 6,582,357 B2 | 6/2003 | Ouchi et al. | |
| 6,589,316 B1 | 7/2003 | Schultz et al. | |
| D481,126 S | 10/2003 | Hayamizu | |
| 6,645,197 B2 | 11/2003 | Garrison et al. | |
| D484,594 S | 12/2003 | Hayamizu | |
| D486,910 S | 2/2004 | Hayamizu et al. | |
| 6,695,772 B1 | 2/2004 | Bon et al. | |
| 6,699,185 B2 | 3/2004 | Gminder et al. | |
| 6,712,479 B1 | 3/2004 | Seitzinger et al. | |
| 6,712,757 B2 | 3/2004 | Becker et al. | |
| 6,712,759 B2 | 3/2004 | Muller | |
| 6,752,755 B2 | 6/2004 | Akiba | |
| 6,755,782 B2 | 6/2004 | Ogawa | |
| D493,529 S | 7/2004 | Hayamizu et al. | |
| 6,764,445 B2 | 7/2004 | Ramans et al. | |
| 6,780,516 B2 | 8/2004 | Chen | |
| 6,783,845 B2 | 8/2004 | Zhang et al. | |
| D498,846 S | 11/2004 | Hayamizu et al. | |
| 6,814,697 B2 | 11/2004 | Ouchi | |
| 6,857,436 B2 | 2/2005 | Labib et al. | |
| 6,882,236 B2 | 4/2005 | Dinn et al. | |
| 6,889,400 B2 | 5/2005 | Kawazoe et al. | |
| 6,921,362 B2 | 7/2005 | Ouchi | |
| 6,921,380 B1 | 7/2005 | Epstein et al. | |
| 6,977,053 B2 | 12/2005 | Mukasa et al. | |
| 6,984,204 B2 | 1/2006 | Akiba | |
| 6,989,183 B2 | 1/2006 | McKillip | |
| 7,074,180 B2 | 7/2006 | Bertolero et al. | |
| 7,080,641 B2 | 7/2006 | Gomez | |

(56) References Cited

U.S. PATENT DOCUMENTS

| | | | |
|---|---|---|---|
| 7,150,713 | B2 | 12/2006 | Shener et al. |
| D534,655 | S | 1/2007 | Iranyi et al. |
| D535,743 | S | 1/2007 | Williams |
| 7,169,167 | B2 | 1/2007 | Chu |
| 7,198,599 | B2 | 4/2007 | Goto et al. |
| 7,223,231 | B2 | 5/2007 | Akiba |
| 7,250,028 | B2 | 7/2007 | Julian et al. |
| 7,270,670 | B1 | 9/2007 | Yencho |
| 7,341,556 | B2 | 3/2008 | Shalman |
| D573,711 | S | 7/2008 | Johnson et al. |
| 7,413,543 | B2 | 8/2008 | Banik et al. |
| D600,807 | S | 9/2009 | Dienst et al. |
| D613,403 | S | 4/2010 | Poll et al. |
| 7,803,109 | B2 | 9/2010 | Gomez |
| 7,803,144 | B1 | 9/2010 | Vollrath |
| 7,927,271 | B2 | 4/2011 | Dimitriou et al. |
| 8,047,215 | B1 | 11/2011 | Sasaki |
| 8,062,214 | B2 | 11/2011 | Shener et al. |
| 8,075,481 | B2 | 12/2011 | Park et al. |
| 8,096,944 | B2 | 1/2012 | Harrel |
| 8,226,549 | B2 | 7/2012 | Kumar et al. |
| 8,419,624 | B2 | 4/2013 | James et al. |
| 8,545,395 | B2 | 10/2013 | Akahoshi et al. |
| 2001/0011162 | A1 | 8/2001 | Epstein |
| 2002/0022762 | A1 | 2/2002 | Beane et al. |
| 2002/0058858 | A1 | 5/2002 | Ogura et al. |
| 2002/0072652 | A1 | 6/2002 | Berci et al. |
| 2002/0091304 | A1 | 7/2002 | Ogura et al. |
| 2002/0193806 | A1 | 12/2002 | Moenning et al. |
| 2003/0200738 | A1 | 10/2003 | Booth |
| 2004/0034339 | A1 | 2/2004 | Stoller et al. |
| 2004/0059363 | A1 | 3/2004 | Alvarez et al. |
| 2004/0082915 | A1 | 4/2004 | Kadan |
| 2004/0204671 | A1 | 10/2004 | Stubbs et al. |
| 2005/0043683 | A1 | 2/2005 | Ravo |
| 2005/0059981 | A1 | 3/2005 | Poll |
| 2005/0065405 | A1 | 3/2005 | Hasegawa |
| 2005/0113797 | A1 | 5/2005 | Ott et al. |
| 2005/0119528 | A1 | 6/2005 | Weinberg |
| 2005/0137529 | A1 | 6/2005 | Mantell |
| 2005/0154355 | A1 | 7/2005 | Gross et al. |
| 2005/0159765 | A1 | 7/2005 | Moutafis et al. |
| 2005/0171467 | A1 | 8/2005 | Landman |
| 2005/0171528 | A1 | 8/2005 | Sartor et al. |
| 2005/0203342 | A1 | 9/2005 | Kucklick et al. |
| 2005/0234301 | A1 | 10/2005 | Gomez |
| 2005/0261553 | A1 | 11/2005 | Swain et al. |
| 2006/0020165 | A1 | 1/2006 | Adams |
| 2006/0041186 | A1 | 2/2006 | Vancaillie |
| 2006/0047184 | A1 | 3/2006 | Banik et al. |
| 2006/0052661 | A1 | 3/2006 | Gannot et al. |
| 2006/0069306 | A1 | 3/2006 | Banik et al. |
| 2006/0252993 | A1 | 11/2006 | Freed et al. |
| 2006/0270910 | A1 | 11/2006 | Davis |
| 2007/0203474 | A1 | 8/2007 | Ryan et al. |
| 2007/0225664 | A1* | 9/2007 | Schultz et al. ............... 604/315 |
| 2007/0282253 | A1 | 12/2007 | Sasaki |
| 2007/0289449 | A1 | 12/2007 | Roberts et al. |
| 2007/0299310 | A1 | 12/2007 | Phillips |
| 2008/0021277 | A1 | 1/2008 | Stefanchik et al. |
| 2008/0051631 | A1 | 2/2008 | Dejima et al. |
| 2008/0081948 | A1 | 4/2008 | Weisenburgh et al. |
| 2008/0086704 | A1 | 4/2008 | Aravamudan |
| 2008/0108871 | A1 | 5/2008 | Mohr |
| 2008/0161646 | A1 | 7/2008 | Gomez |
| 2008/0188715 | A1 | 8/2008 | Fujimoto |
| 2008/0200765 | A1 | 8/2008 | Mondschein |
| 2008/0208128 | A1 | 8/2008 | Guo et al. |
| 2008/0249362 | A1 | 10/2008 | Jiang et al. |
| 2008/0319266 | A1* | 12/2008 | Poll et al. ................. 600/157 |
| 2009/0018602 | A1 | 1/2009 | Mitelberg et al. |
| 2009/0113644 | A1 | 5/2009 | Heck |
| 2009/0215018 | A1 | 8/2009 | Edmondson et al. |
| 2009/0253962 | A1 | 10/2009 | Fernandez et al. |
| 2009/0253965 | A1 | 10/2009 | Miyamoto |
| 2010/0168520 | A1 | 7/2010 | Poll et al. |
| 2010/0198014 | A1 | 8/2010 | Poll et al. |
| 2012/0022331 | A1 | 1/2012 | Poll et al. |
| 2012/0101337 | A1 | 4/2012 | Clark et al. |
| 2012/0184897 | A1 | 7/2012 | Poll |
| 2012/0197084 | A1 | 8/2012 | Drach et al. |
| 2012/0310147 | A1 | 12/2012 | Poll et al. |
| 2014/0114128 | A1 | 4/2014 | Wills |
| 2015/0005582 | A1 | 1/2015 | Poll et al. |

FOREIGN PATENT DOCUMENTS

| | | |
|---|---|---|
| JP | 59-203534 | 11/1984 |
| JP | 61-168328 | 7/1986 |
| JP | 05-199979 | 8/1993 |
| JP | 09-135804 | 5/1997 |
| JP | 2000-225093 | 8/2000 |
| JP | 2005-110978 | 4/2005 |
| WO | WO92/10969 A1 | 7/1992 |
| WO | WO92/22238 A1 | 12/1992 |
| WO | WO2005/009227 A1 | 2/2005 |
| WO | WO2006/014814 A1 | 2/2006 |
| WO | WO2008/030256 A1 | 3/2008 |
| WO | WO2008/077080 A2 | 6/2008 |
| WO | WO2008/128142 A2 | 10/2008 |
| WO | WO2008/130582 A2 | 10/2008 |
| WO | WO2009/073577 A2 | 6/2009 |
| WO | WO2010/042913 A2 | 4/2010 |
| WO | WO2010/042915 A2 | 4/2010 |
| WO | WO2011/041387 A1 | 4/2011 |
| WO | WO2011/044448 A2 | 4/2011 |
| WO | WO2011/130399 A1 | 10/2011 |
| WO | WO2012/005819 A1 | 1/2012 |
| WO | WO2012/044410 A2 | 4/2012 |
| WO | WO2012/122263 A2 | 9/2012 |

OTHER PUBLICATIONS

Hashimoto et al.; Development of a fogless scope and its analysis using infrared radiation pyrometer; Surg Endosc; 11(8); pp. 805-808; Aug. 1997.

Lawrentschuk et al.; Laparoscopic lens fogging: A review of etiology and methods to maintain a clear visual field; Journal of Endourology; 24(6); pp. 905-913; Jun. 2010.

Ohdaira et al.; Antifogging effects of a socket-type device with the superhydrophilic, titanium dioxide coated glass for laparoscope; Surg endosc; 21(2); pp. 333-338; Dec. 2007.

Ott, Douglas E.; Chapter 1. Pneumoperitoneum: Production, management, effects and consequences; in Prevention & Management of Laparoendoscopic Surgical Complications, 1st Ed.; 6 pgs.; Jan. 1999 (retrieved from: http://laparoscopy.blogs.com/prevention_management/2006/02/chapter_1_pneum.html on Oct. 7, 2013).

Poll et al.; Design U.S. Appl. No. 29/329,224 entitled "Manifold Coupling," filed Dec. 10, 2008 (now abandoned).

Poll et al.; Design U.S. Appl. No. 29/329,225 entitled "Sheath Manifold for Maintaining Surgical Scope Visualization," filed Dec. 10, 2008 (now abandoned).

Poll et al.; Design U.S. Appl. No. 29/329,221 entitled "Handle for Maintaining Surgical Scope Visualization," filed Dec. 10, 2008 (now abandoned).

Poll et al.; Design U.S. Appl. No. 29/335,699 entitled "Surgical Scope Stabilizer," filed Apr. 20, 2009 (now abandoned).

Poll et al.; U.S. Appl. No. 14/308,644 entitled "Sheath for hand-held and robotic laparoscopes," filed Jun. 18, 2014.

* cited by examiner

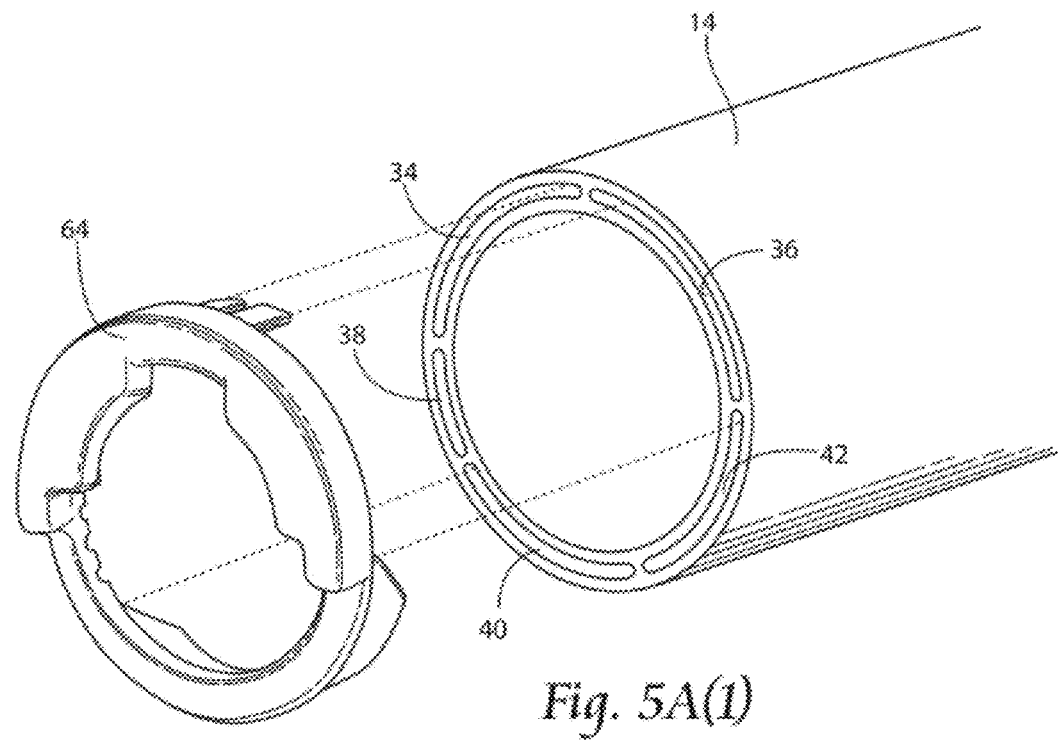
Fig. 5A(1)
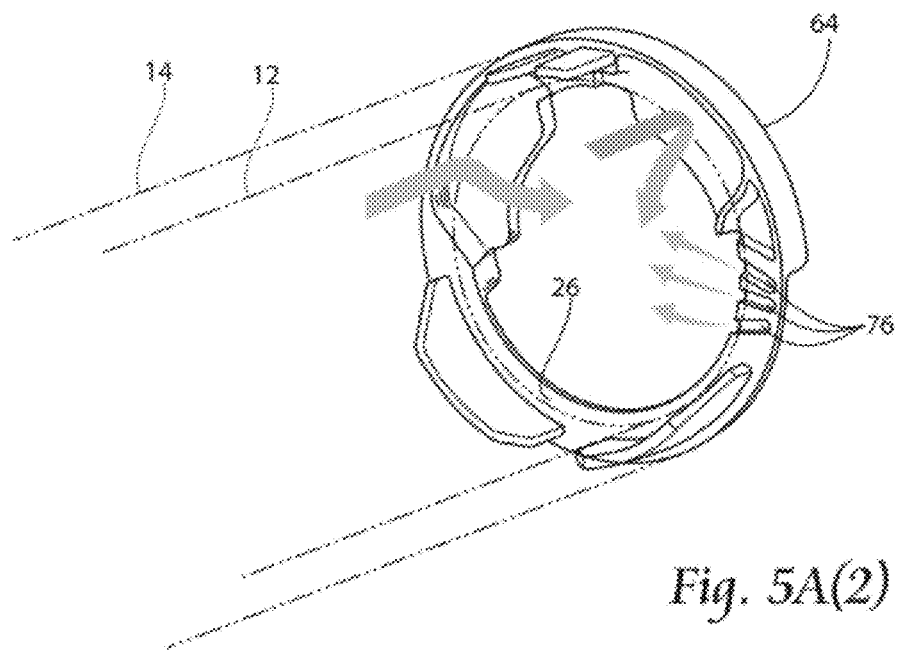
Fig. 5A(2)

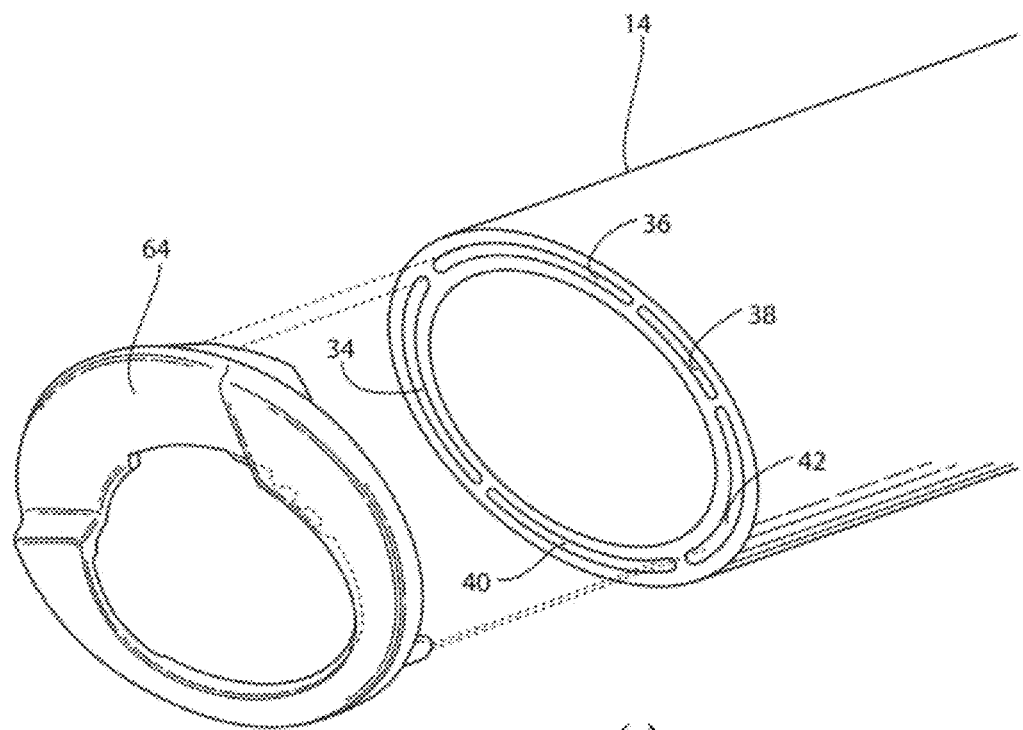
Fig. 5B(1)
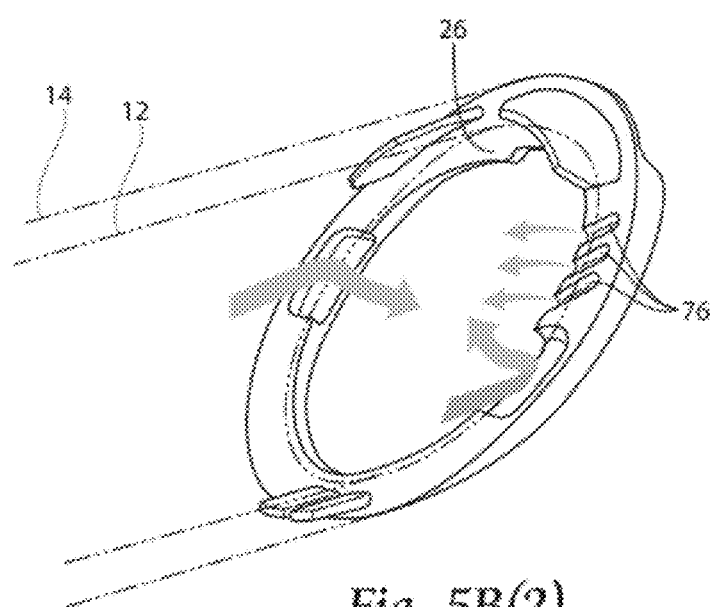
Fig. 5B(2)

SYSTEMS AND METHODS FOR OPTIMIZING AND MAINTAINING VISUALIZATION OF A SURGICAL FIELD DURING THE USE OF SURGICAL SCOPES

RELATED APPLICATION

This application is a continuation-in-part of co-pending U.S. patent application Ser. No. 13/004,505, filed Jan. 11, 2011, entitled "Systems and Methods for Optimizing and Maintaining Visualization of a Surgical Field During the Use of Surgical Scopes," which claims the benefit of U.S. Provisional Patent Application Ser. No. 61/335,712, filed Jan. 11, 2010, and entitled "Systems and Methods for Optimizing and Maintaining Visualization of a Surgical Field During the Use of Surgical Scopes," which are each incorporated herein by reference.

FIELD OF THE INVENTION

The invention generally relates to surgical scopes, and, more particularly, for optimizing and maintaining visualization of a surgical field when using a surgical scope, such as, e.g., a laparoscope.

BACKGROUND OF THE INVENTION

Minimally invasive surgical procedures utilizing surgical scopes are desirable because they often provide one or more of the following advantages: reduced blood loss; reduced post-operative patient discomfort; shortened recovery and hospitalization time; smaller incisions; and reduced exposure of internal organs to possible contaminants.

Generally, minimally invasive surgeries utilize scopes, such as laparoscopes, that permit remote visualization of a surgical site within a patient's body while the surgical procedure is being performed. During a laparoscopic procedure, the patient's abdominal or pelvic cavity is accessed through two or more relatively small incisions rather than through a single large incision that is typical in a conventional surgery. Surgical scopes, such as laparoscopes, usually consist in part of a rigid or relatively rigid rod or shaft having an objective lens at one end and an eyepiece and/or integrated visual display at the other. The scope may also be connected to a remote visual display device or a video camera to record surgical procedures.

In laparoscopic surgeries, the abdomen is typically inflated with a gas through the use of an insufflator, to distend the abdominal space by elevating the abdominal wall above the internal organs and thereby create a sufficient working and viewing space for the surgeon. Carbon dioxide is usually used for insufflation, though other suitable gases may also be used. Conventional insufflators are adapted to cycle on and off to maintain a preset and suitable pressure within the patient's body cavity.

The local environment within a patient's abdominal space is generally rather warm and humid, and the use of devices such as harmonic scalpels and other cutting and coagulating devices generate mist, smoke, and other debris that is released into the surgical field and often becomes suspended throughout the expanded abdominal space. Additionally, blood, bodily fluids, pieces of tissue, fat or other bodily material may come in contact with or even attach to the lens. As a result of these conditions, visualization through the scope can be significantly diminished. Typically, the only solution to fogging and debris collection on the lens is removal of the scope from the body cavity and defogging or cleaning the lens by wiping it with a cloth, warming the scope tip, or utilizing another defogging method. The need to remove the scope to defog and remove debris from the lens is inconvenient for the scope operator and the surgeon and can interrupt and undesirably prolong surgical procedures.

SUMMARY OF THE INVENTION

One aspect of the invention provides a condition system for air that, in use, is passed across a laparoscopic lens to maintain visualization of an operating cavity. The system comprises an access device that is sized and configured to provide communication with an insufflated $CO_2$ environment within the operating cavity. The system also comprises an air conditioning set, which is sized and configured to couple to the access device and to a view optimizing sheath sized and configured to direct air across the laparoscopic lens. The system also includes an air conditioning driver, which interacts with the air conditioning set to convey air from the access device and through the air conditioning set for passage through the view optimizing sheath and across the laparoscopic lens. The system maintains visualization of the operating cavity through the laparoscopic lens independent of operation of the insufflator circuit.

In one embodiment, the air conditioning set is sized and configured to selectively couple and decouple from the air conditioning driver. In this arrangement, the air conditioning set can be disposable, and the air conditioning driver can be reusable.

In one embodiment, the air conditioning set includes an air moving component and an air treatment component that removes at least one undesired agent, such as smoke, particulates, pathogens, odors, and toxins, e.g., by filtration. The air conditioning set can also include a moisture removing element.

In one embodiment, the air conditioning set includes inlet tubing sized and configured to couple with the access device and outlet tubing sized and configured to couple with the view optimizing sheath. In this arrangement, at least one of the inlet and outlet tubing includes a moisture trap. Desirably, the moisture trap is located adjacent to the access device.

Another aspect of the invention provides a method for optimizing visualization through a laparoscopic lens. The method comprises (i) operating an insufflator circuit to insufflate an operating cavity with $CO_2$; (ii) visualizing the operating cavity insufflated with $CO_2$ through a laparoscopic lens; (iii) independent of (i), operating an air condition system having the technical features just described, to convey $CO_2$ from the operating cavity through an air flow path outside the operating cavity; and (iv) passing $CO_2$ conveyed during (iii) across the laparoscopic lens to maintain visualization of the operating cavity.

In one embodiment, the method includes, during (iii), removing at least one undesired agent from the air flow path.

In one embodiment, the method includes, during (iii), removing water vapor from the air flow path.

The systems and methods provide a closed loop air conditioning system that operates independent of an insufflation circuit to optimize visualization through a laparoscopic lens. The pressure of air delivered by the closed loop air conditioning systems and methods is not constrained by the insufflations pressure (which is typically about 15 mmHg), but can be adjusted to further optimize the laparoscopic view optimizing functions. For example, the pressure of air delivered for the view optimizing function by the air conditioning systems and methods can be increased well above typical insufflation pressure, if desired, e.g., to a range of between 1 PSI and 5

PSI, to provide enhanced defogging and debris removal. Further, the air delivered by the closed loop air conditioning systems and methods can be delivered continuously, even when the insufflations circuit is in an off-cycle. The closed loop air conditioning systems and methods can also serve to beneficially process or treat the air drawn from the insufflated CO2 environment present in the operating cavity, to remove, e.g., smoke, particulates, aerosolized pathogens, and water vapor from the airflow before it is conducted by the view optimizing function across the lens of the laparoscope.

BRIEF DESCRIPTION OF THE DRAWINGS

FIGS. 5A(1) and 5A(2) are enlarged, exploded views of the deflector assembly for use with a laparoscope having a 0° shaft tip.

FIGS. 5B(1) and 5B(2) are enlarged, exploded views of the deflector assembly for use with a laparoscope having an angled shaft tip.

DESCRIPTION OF THE PREFERRED EMBODIMENTS

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. View Optimizing Assembly

A. Overview

Figures 1A, 1B:
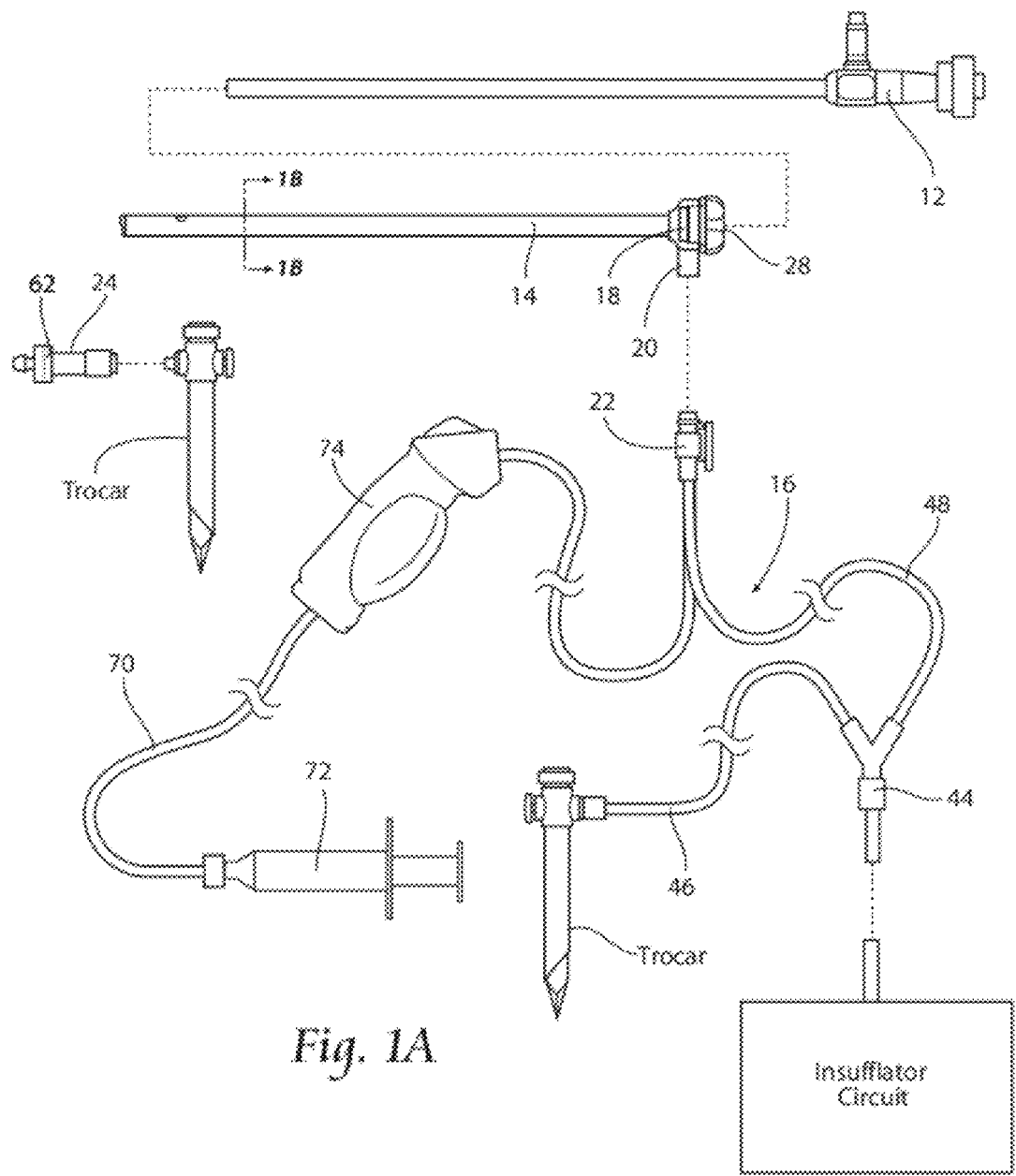
FIG. 1A is a somewhat schematic view of a view optimizing assembly for use with a laparoscope having a 0° shaft tip.
FIG. 1B is a section view of the sheath, showing internal fluid flow lumens, taken generally along line 1B-1B in FIG. 1A.
Figure 2A:
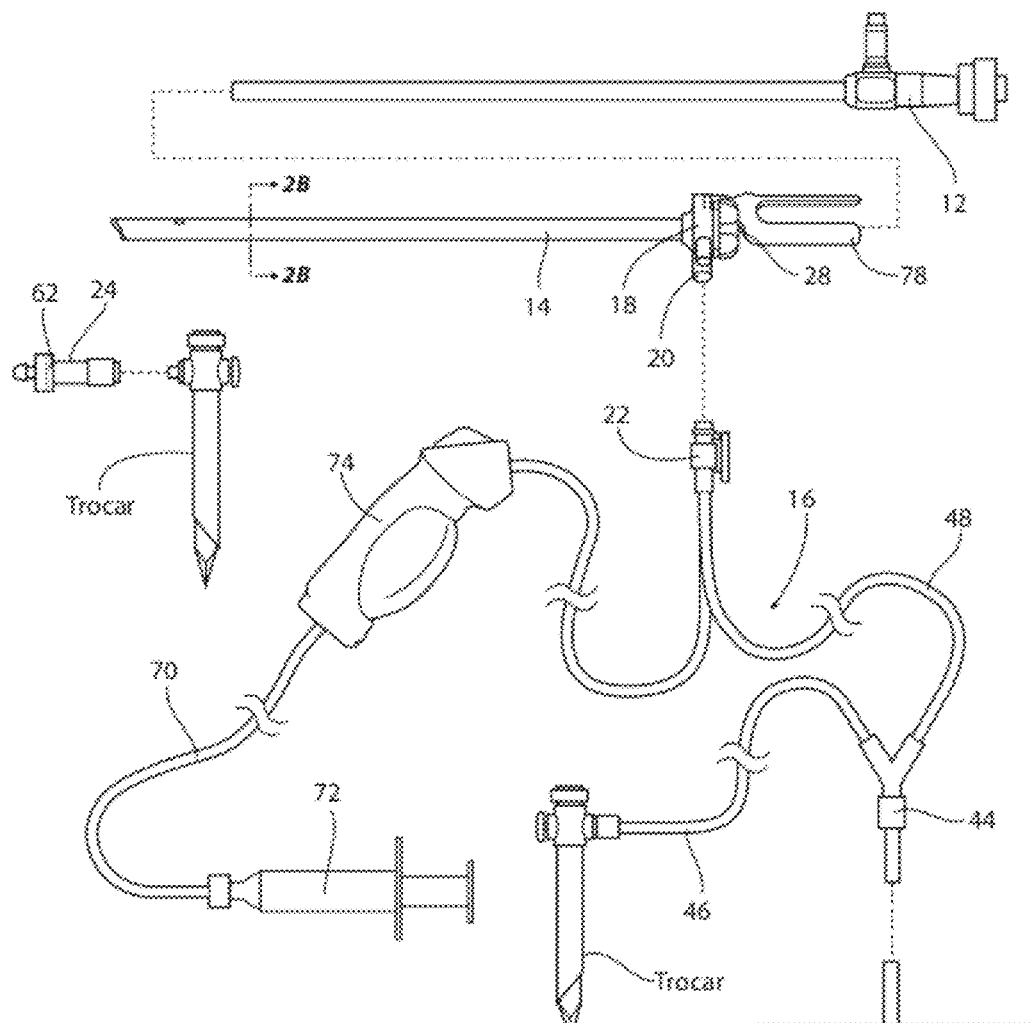
FIG. 2A is a somewhat schematic of a view optimizing assembly for use with a laparoscope having an angled shaft tip.

FIGS. 1A/1B and FIG. 2A/2B show a view optimizing assembly 10 for use in association with a state of the art laparoscope 12. In FIGS. 1A/1B, the laparoscope 12 possesses at 0° (blunt) shaft tip In FIGS. 2A/2B, the laparoscope possess an angle shaft tip (e.g., a 30° shaft tip or 45° shaft tip). The components of the view optimizing assembly 10 may be made from plastic materials (extruded and/or molded), but other suitable materials, such as metal or a composite material, or combinations thereof could be used.

As will be described in greater detail, the view optimizing assembly 10 facilitates intra-operative defogging, surgical debris deflection, and cleaning of a laparoscope lens during minimally invasive surgery, while also maintaining visualization of the surgical site. The view optimizing assembly 10 is intended to be a single-use, disposable laparoscopic accessory. The view optimizing assembly 10 is desirably a sterile accessory for immediate set up and use on a sterile operating field.

As shown in FIGS. 1A and 2A, the view optimizing assembly 10 comprises a multi-lumen sheath assembly 14, which mounts over the shaft of the laparoscope 12. The end of the shaft is sized and configured to match the size and configuration of the corresponding laparoscope 12, having a blunt tip in FIG. 1A and angled tip in FIG. 2A. The assembly 10 includes a tubing set 16 to connect the sheath 14 to an existing anhydrous carbon dioxide (CO2) insufflation circuit.

In use, the view optimizing assembly 10 makes possible the practice of a surgical method for maintaining clear visualization of the surgical site without removing the laparoscope 12 from the abdominal cavity for the purpose of cleaning or de-fogging its lens. Furthermore, the view optimizing assembly 10 also makes possible a surgical method for maintaining clear visualization that includes the ability to make a quick exchange of laparoscopes having different operating characteristics (e.g., laparoscopes with different tip angles, lengths, or diameters) entirely on the sterile operating field and without interference with the preexisting surgical set-up on the sterile operating field. The view optimizing assembly 10 integrates with the existing suite of minimally invasive instrumentation. It does not interfere with the surgical set-up, and it requires minimal change in the process or practice of a surgical operating room (OR) team.

Figure 7:
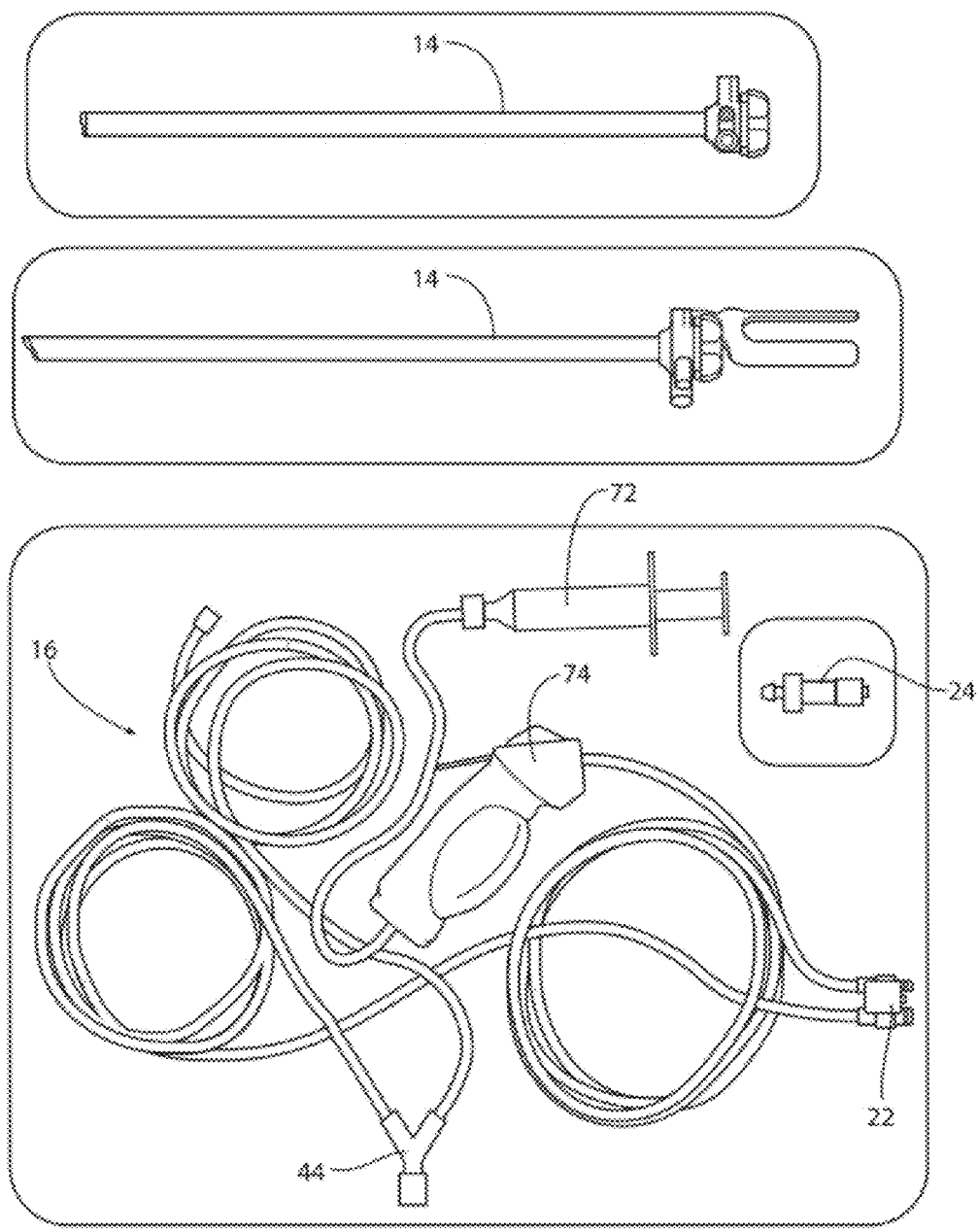
FIGS. 7 to 34 illustrate a representative method including the set up and use of the view optimizing assembly using sterile technique by technicians/operating room personnel.

The view optimization assembly 10 desirably comes packaged for use in sterile peel away pouches (see FIG. 7). As also shown in FIGS. 1A and 2A, the pouches contain the components of the view optimization assembly 10, including the sheath 14 and a manifold 18 that is assembled to the sheath 14 and that includes a quick exchange coupling 20; the tubing set 16 which includes a quick exchange coupler 22 that mates with the quick exchange coupling 20 on the manifold 18; and (optionally) a vent device 24.

B. The Sheath/Manifold Assembly

As shown in FIGS. 1A and 2A, the sheath 14/manifold 18 assembly includes a sheath 14 that is sized and configured to receive a laparoscope 12 having a prescribed tip angle, length, and diameter. The sheath 14 includes a stop 26 (see FIGS. 5A(2) and 5B(2)) formed adjacent the distal end of the sheath 14. The stop 26 prevents advancement of the laparoscope 12 beyond the distal end of the sheath 14, so that lens at the distal end of the laparoscope 12 rests in a desired, generally coterminous alignment with the distal end of the sheath 14. The sheath 14 also includes a locking collar 28 at its proximal end to frictionally engage the laparoscope 12 and resist axial withdrawal of the laparoscope 12 from the sheath 14.

Figure 14:
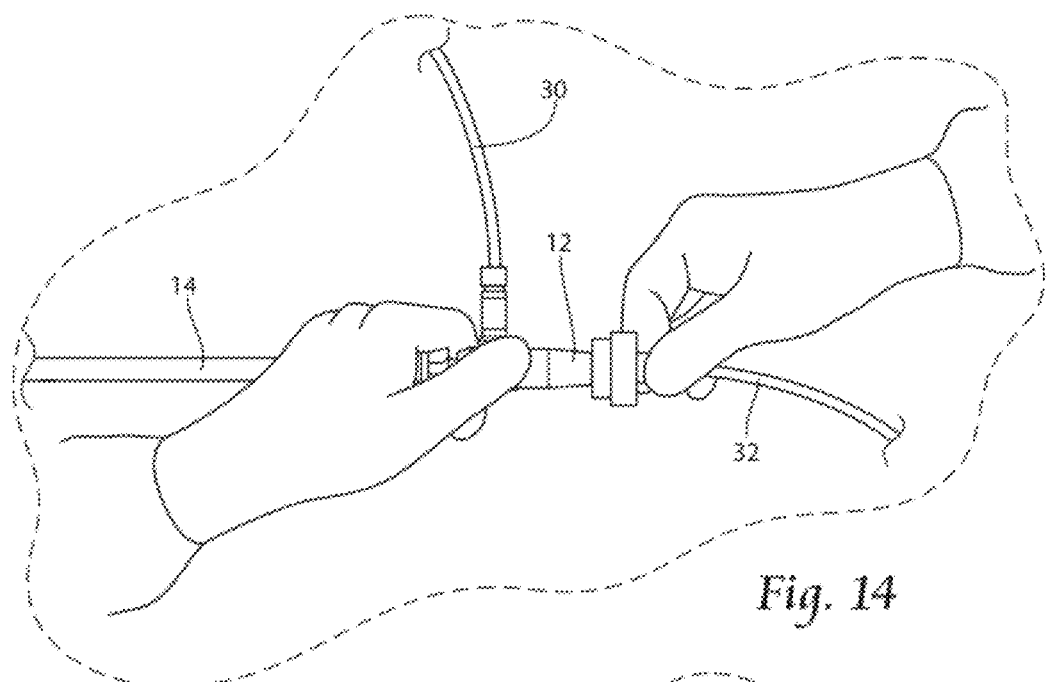

In use, it is expected that the laparoscope 12 will be inserted into the sheath 14 by a scrub nurse during set-up for the operation (see FIGS. 8 to 11). The assembled laparoscopic and sheath 14 will then be handed as a unit to personnel at the operating room (OR) table at the desired time). The laparoscope 12 is then connected by personnel at the OR table in conventional fashion to a light cable 30 (which directs light to illuminate the operative field) and the camera cable 32 (which takes the image from the scope and displays it on monitors in the OR) (see FIG. 14). The sheath 14 is sized and configured not to interfere with this normal set-up of the laparoscope 12.

Figure 16:
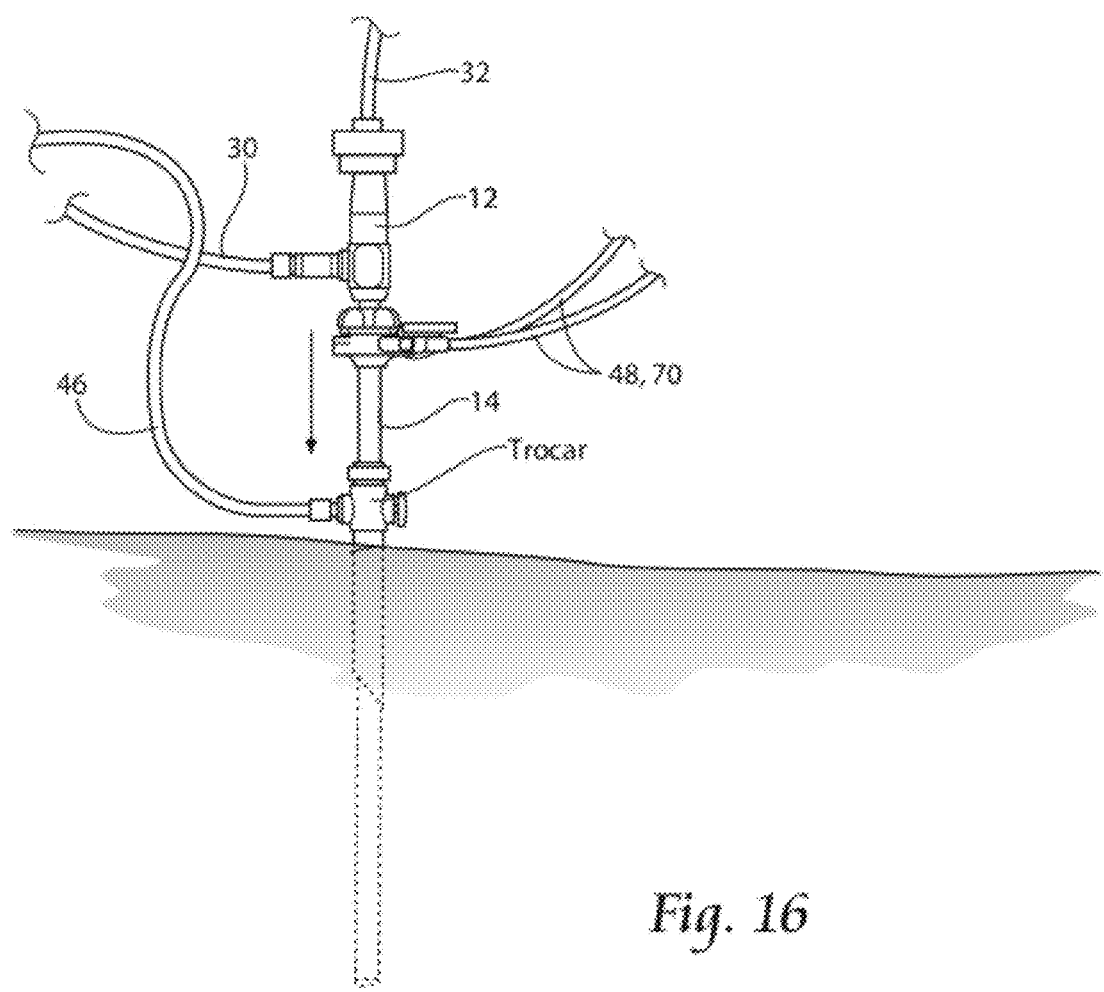

In use, the assembled laparoscopic and sheath 14 are placed as a unit through a trocar into the body cavity (e.g., the abdominal cavity), for viewing the surgical procedure as it is performed (see FIG. 16).

Figure 2B:
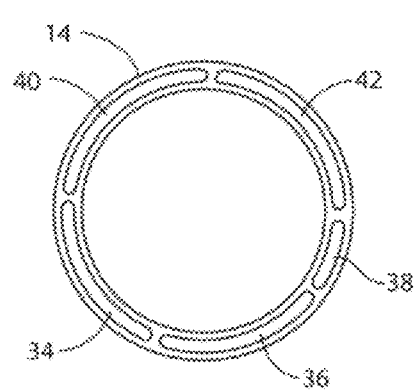
FIG. 2B is a section view of the sheath, showing internal fluid flow lumens, taken generally along line 2B-2B in FIG. 2A.
Figure 3A:
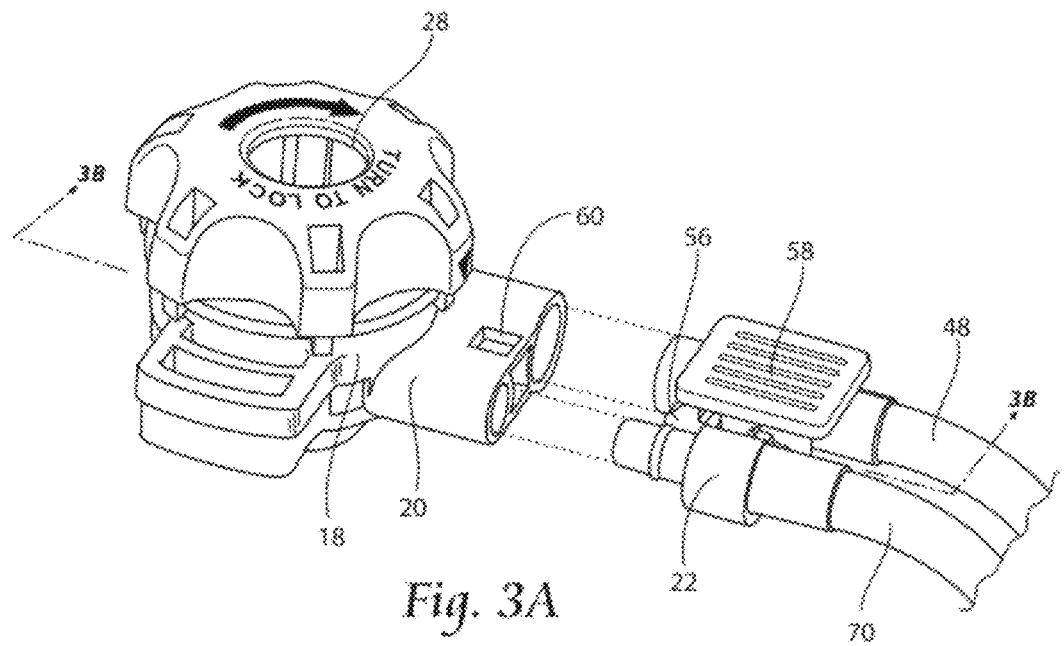
FIG. 3A is an enlarged perspective view of a manifold that the view optimizing assembly shown in FIG. 1A or FIG. 2A incorporates, including a quick exchange coupling, and a quick exchange coupler that the tubing set shown in FIG. 1A or FIG. 2A incorporates, the coupling and the coupler being disconnected.

As shown in FIGS. 1A and 2A, and as further shown in FIG. 3A, the sheath 14/manifold 18 assembly also includes the manifold 18 at the proximal end of the sheath 14. The manifold 18 communicates with multiple lumens (five 34 to 42) are shown in the illustrated embodiment) formed within the wall of the sheath 14 (see FIGS. 1B and 2B. In use, the lumens 34 to 42 convey anhydrous CO2 to the distal end of the sheath 14; vent or exhaust air from the distal end of the sheath 14 through the manifold 18; and, if desired, convey sterile fluid and bursts of air to the distal end of the sheath 14. In a representative embodiment (see FIGS. 1B and 2B), two lumens 34 and 36 are dedicated to the transport of CO2; two lumens 40 and 42 are dedicated to venting; and one lumen 38 is dedicated to the transports of sterile fluid or air.

C. The Tubing Set

As previously described, the tubing set 16 includes a quick exchange coupler 22 that mates with the quick exchange coupling 20 on the manifold 18 (see FIGS. 3A/3B and 4A/4B). The tubing set 16 includes lengths of flexible medical grade tubing with individual end couplers (best shown in FIGS. 1A and 2A) that connect to an existing CO2 insufflation circuit and, if desired, a source of sterile fluid (saline or sterile water, preferably with a "surface active agent") on the sterile operating field (e.g., a bag or a syringe). The tubing set 16 includes a Y-connector 44 that divides the anhydrous CO2 output of the insufflation circuit in a first branch 46 for coupling to an insufflation trocar inserted in the body cavity (as will be described later), and a second branch 48 coupled to the quick exchange coupler 22.

The second branch 48 diverts a small portion of the CO2 output (e.g., 20% or less) to the quick exchange coupler 22.

Figure 3B:
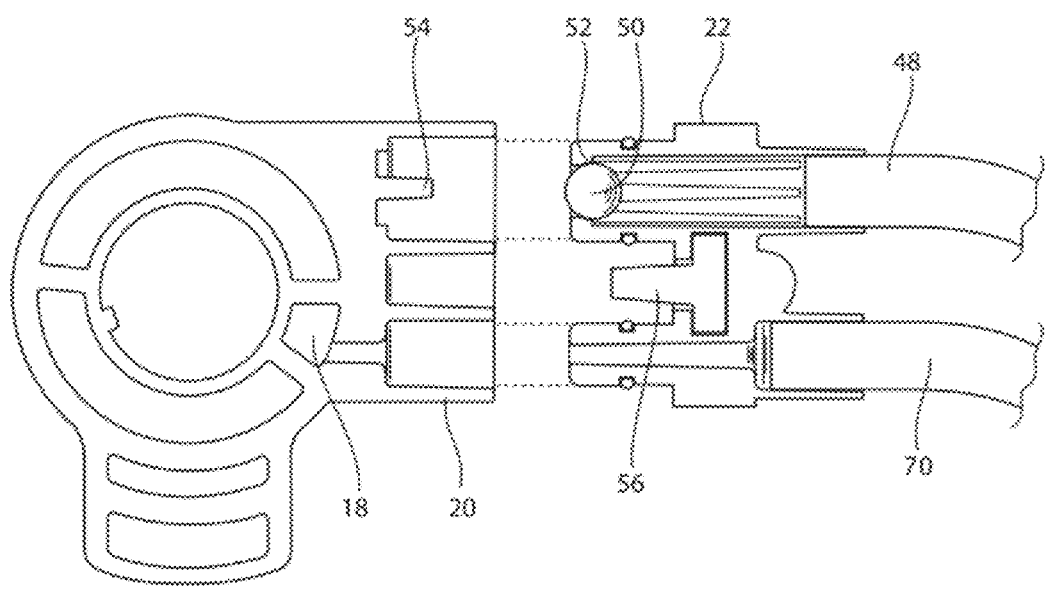
FIG. 3B is a sectional view taken generally along line 3B-3B in FIG. 3A, showing a one way check valve that is normally closed.
Figure 4A:
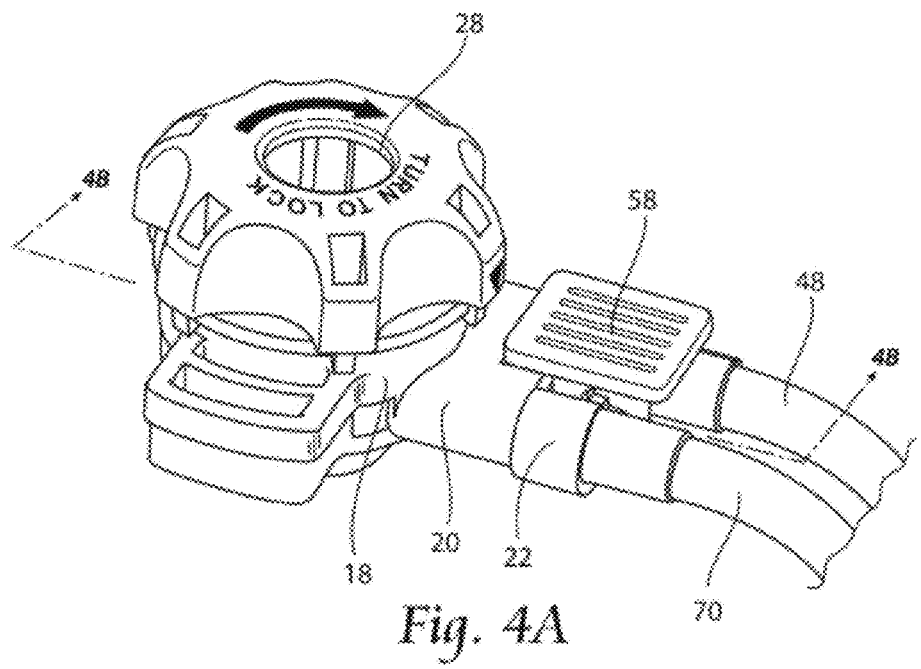
FIG. 4A is an enlarged perspective view of the manifold including a quick exchange coupling and the quick exchange coupler of the tubing set, as shown in FIG. 3A, but now connected.
Figure 4B:
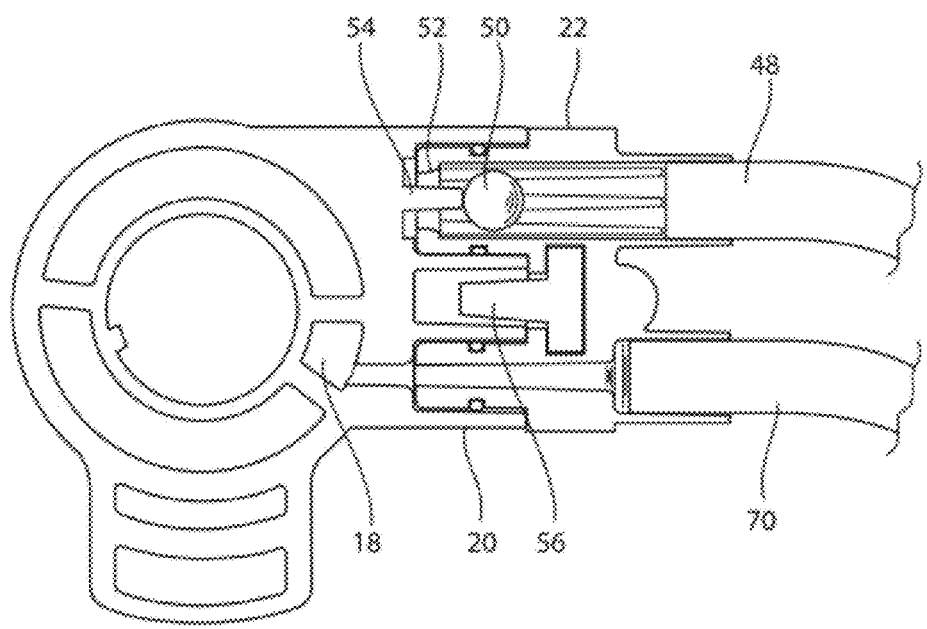
FIG. 4B is a sectional view taken generally along line 4B-4B in FIG. 4A, showing the one way check valve that is opened by the connection of the quick exchange coupling and connectors.

As shown in FIGS. 3B and 4B, the quick exchange coupler 22 includes a one way check valve 50 that communicates with the second branch 48 of the tubing set 16. In the illustrated embodiment, the check valve 50 comprises a ball valve. Insufflation pressure normally presses the ball valve 50 against a ball valve seat 52 (as shown in FIG. 3B). A projection 54 in the manifold 18 displaces the ball valve 50 from the valve seat 52 when the quick exchange coupler 22 mates with the quick exchange coupling 20 on the manifold 18 (as shown in FIG. 4B). Unseating the ball valve 50 opens flow communication through the check valve 50. In the absence of coupling the quick exchange coupler 22 on the tubing set 16 to the quick exchange coupling 20 on the manifold 18, the check valve 50 remains closed, normally blocking flow of CO2 through the second branch 48.

Thus, the tubing set 16 accommodates the set-up of the supply of the entire CO2 output to a insufflation trocar through the tubing set 16, separate and independent of the connection of the tubing set 16 to the manifold 18 of the sheath 14.

As FIGS. 3A and 4A further show, a latch 56 carried on a spring-biased button 58 on the quick exchange coupler 22 "clicks" into a detent 60 on the quick exchange coupling 20 on the manifold 18 to reliably lock the coupler 22 and coupling 20 together for use, opening the check valve to flow CO2 through the second branch 48 (shown in FIGS. 4A/4B). Depressing the button 58 allows the quick exchange coupler 22 and coupling 20 to be separated, and the check valve 50 will close in response to insufflation pressure in the second branch 48 (as shown in FIGS. 3A/3B).

Figure 15:
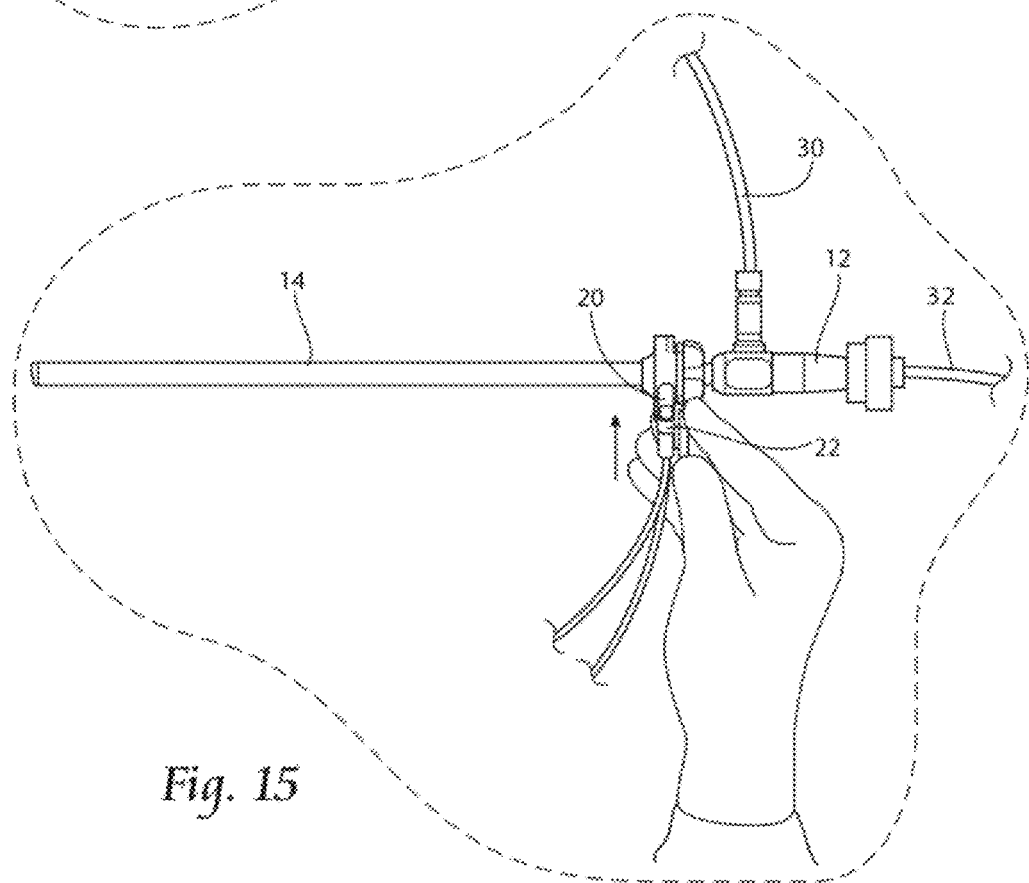
Figure 22:
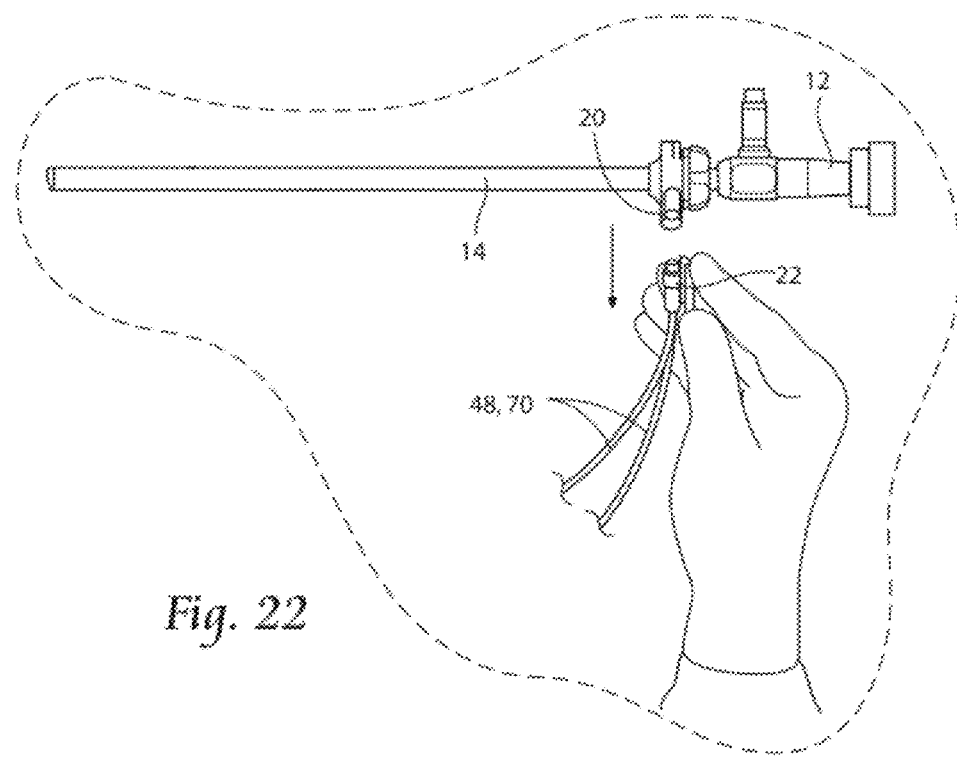
Figure 23:
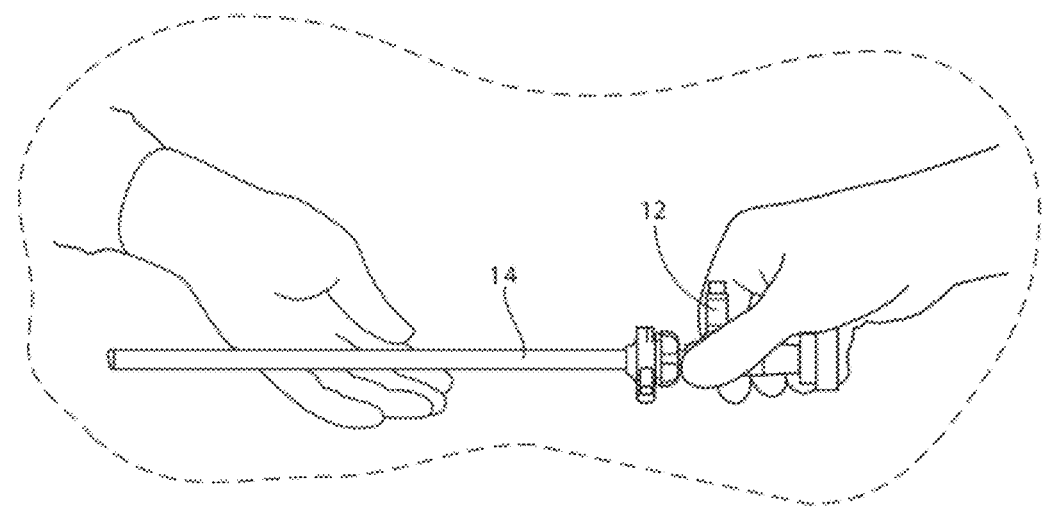
Figure 24:
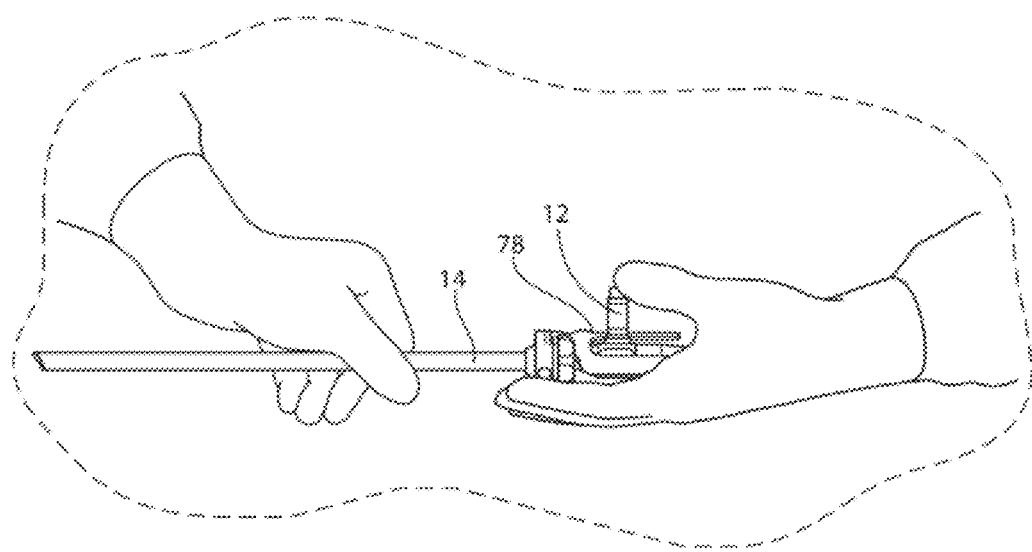
Figure 25:
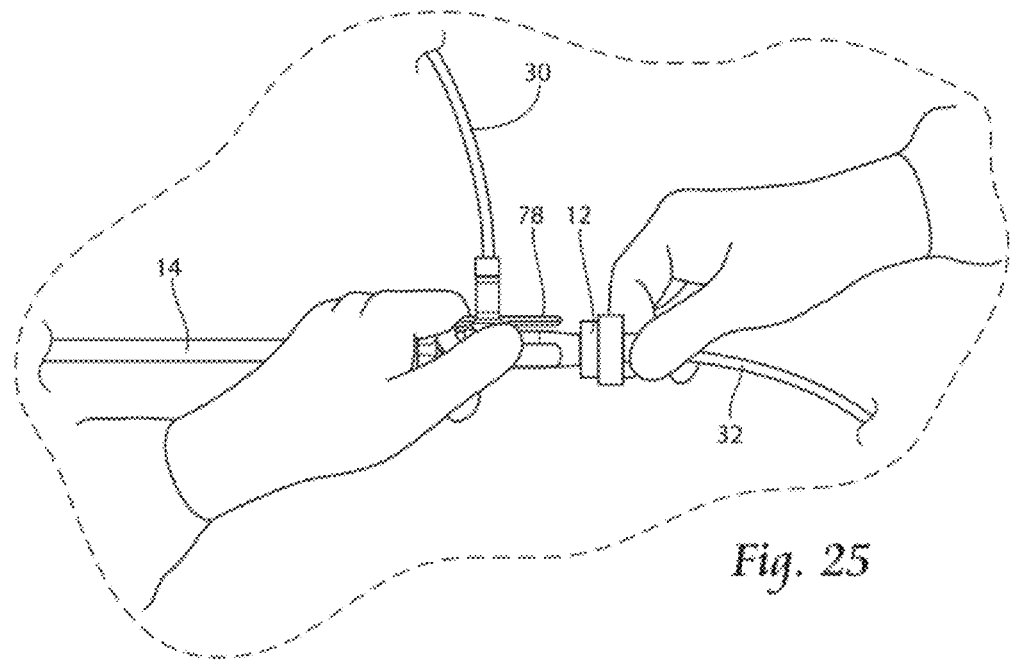
Figure 26:
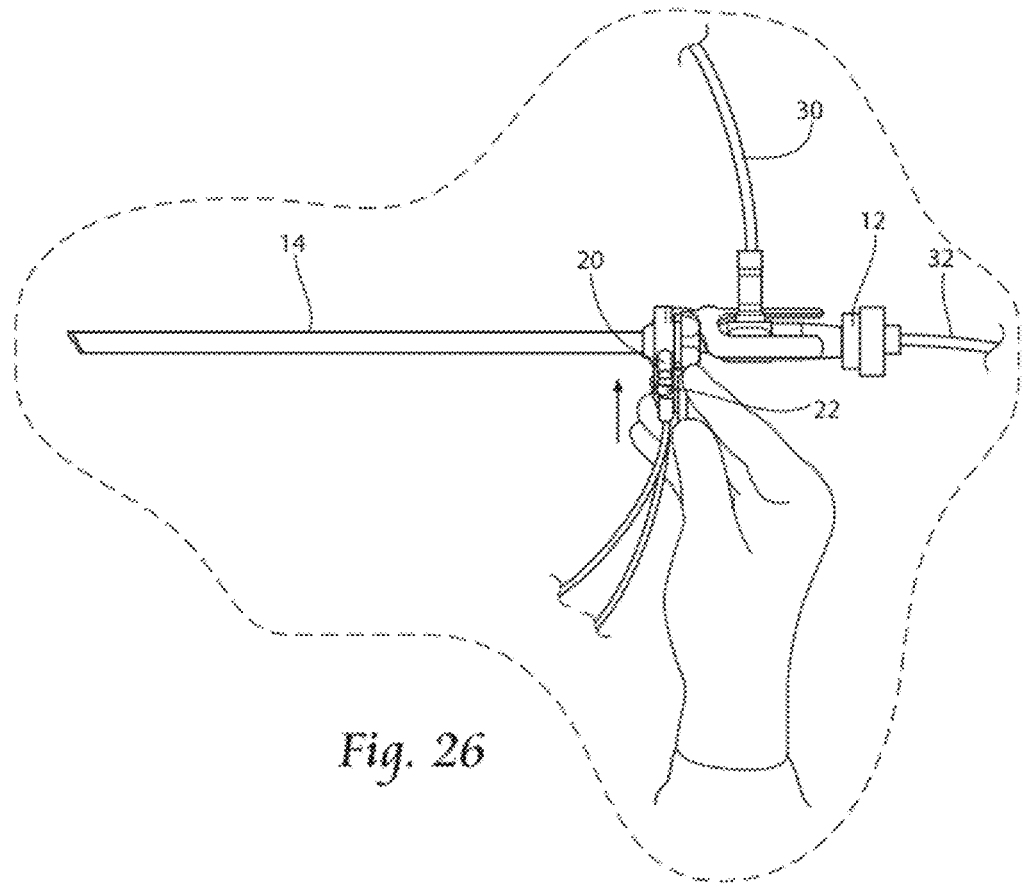
Figure 27:
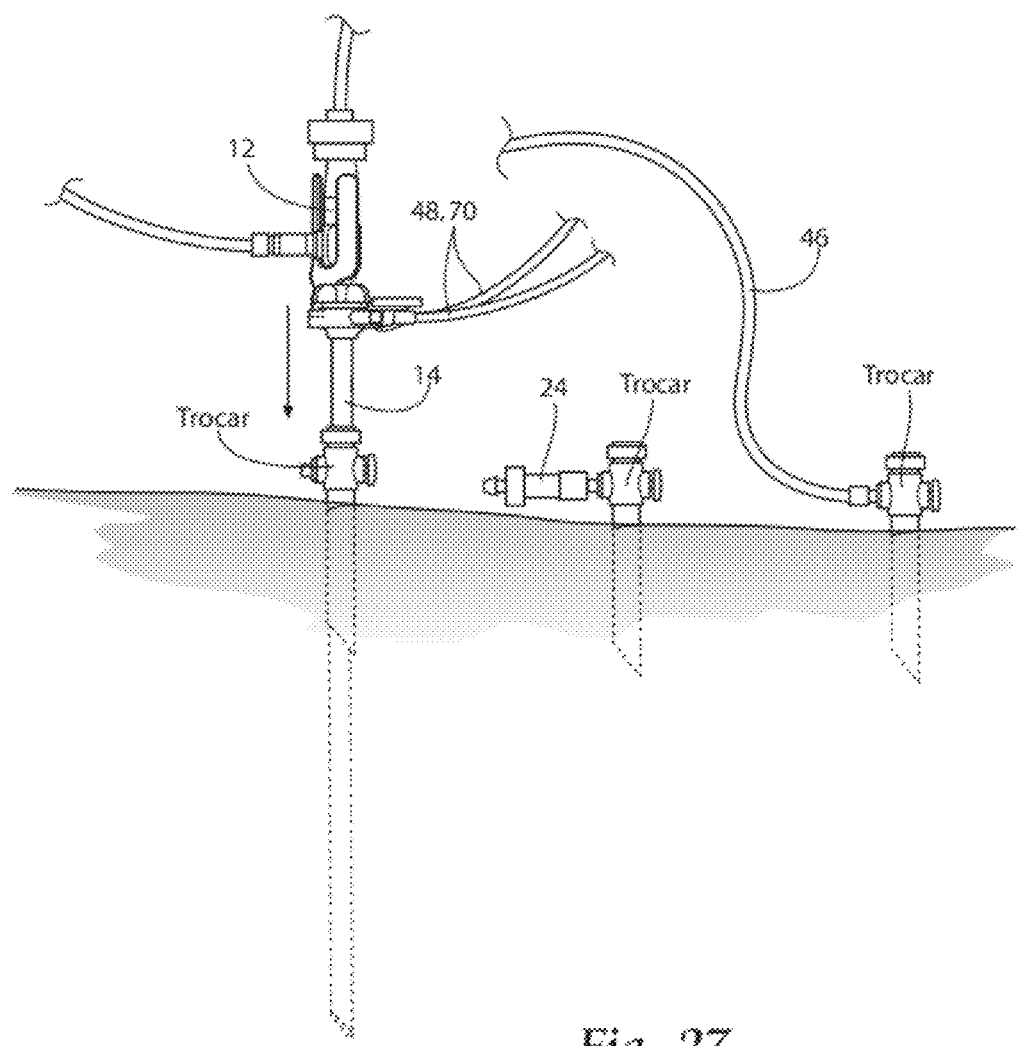

Connection of the quick exchange coupling 20 on the manifold 18 to the quick exchange coupler 22 on the tubing set 16 is intended to occur at the OR table in the normal course, after the laparoscope 12 is connected to the light cable 30 and the camera cable 32 (see FIG. 15). Upon coupling, the one way check valve 50 is opened, and the manifold 18 directs the small portion of CO2 from the CO2 insufflation circuit. Disconnection of the of the quick exchange coupling 20 on the manifold 18 to the quick exchange coupler 22 on the tubing set 16 is also intended to occur at the OR table in the normal course, after a removal and/or exchange of a laparoscope 12 (see FIG. 22).

D. The Vent Device

The vent device 24 (see FIGS. 1A and 2A) comprises a tube with an inline membrane 62 that restricts air flow through the tube. A proximal end of the tube is sized and configured to couple to a stopcock valve of a conventional trocar, as will be described later. In use, the vent device 24 provides a controlled leak of CO2 from the operating cavity, as will also be described in greater detail later.

E. The Deflector Assembly

1. CO2

The sheath 14 includes at its distal end a deflector assembly 64 (see FIGS. 5A(1) and 5A(2) for a blunt shaft tip and FIGS. 5B(1) and 5B(2) for an angled shaft tip). The deflector assembly 64 projects a predetermined distance beyond the distal end of the sheath 14, and thus also a predetermined distance beyond the lens at the distal end of the laparoscope 12. The deflector assembly 64 communicates with the lumens in the sheath 14. The deflector assembly 64 is sized and configured to direct the small portion of the CO2 from the insufflation circuit in a prescribed flow path and flow velocity continuously across the laparoscopic lens.

The desired flow path and flow velocity of CO2 established by the deflector assembly 64 continuously across the laparoscopic lens creates a "wind shear." The wind shear path of anhydrous CO2 prevents fogging. The desired flow path and flow velocity of CO2 established by the deflector assembly 64 continuously across the laparoscopic lens also desirably serves to deflect smoke and surgical debris away from the laparoscopic lens during surgery.

2. Physical, Pneumatic, and Optical Characteristics of the Deflector Assembly

The size and configuration of the deflector assembly 64 are defined and constrained by several, sometime overlapping considerations including (i) prescribed physical characteristics, which are imposed due to the need to access the operating environment in as minimally invasive manner as possible and to be compatible with state of the art laparoscopes and other laparoscopic surgical instruments and techniques; (ii) prescribed pneumatic characteristics, which are imposed due to the need to create a particular "wind shear" effect in terms of the flow path and flow velocity of CO2 across the laparoscopic lens; and (iii) prescribed optical characteristics, which are imposed due to the need to prevent interference with the field of view and the visualization of the operating field by the laparoscope 12.

3. Physical Characteristics

The size and configuration requirements for minimally invasive access compatible with state of the art laparoscopic instrumentation and techniques are paramount. These requirements impose constrains upon the minimum inside diameter of the sheath 14 as well as the maximum outside diameter of the sheath 14. Because state of the art laparoscopes are provided with different shaft diameters, lengths, and lens configurations, the sheath dimensions and configuration change for compatibility with them. The view optimizing assembly 10 actually includes a family of sheath 14/manifold 18 assemblies differently sized and configured to accommodate different classes of laparoscopes, to make possible compatibility with the families of state of the art laparoscopes that are in use.

For example, state of the art laparoscopes include 10 mm laparoscopes, 5 mm laparoscopes, and, within these sizes, 0° shaft tips, 30° shaft tips, and 45° shaft tips. Further, within these classes of laparoscopes, manufacturing tolerances typically vary from scope to scope, as well as from manufacturer to manufacturer. A given sheath 14/manifold 18 assembly for a given laparoscope class (e.g., 10 mm or 5 mm) desirably takes these typical manufacturing and manufacturer variances into account, and is desirably sized and configured to fit the largest scope variance encountered within a given laparoscope class.

To maximize the fluid flow lumen area within the sheath 14, the minimum inside diameter of a given sheath 14 must closely conform to the maximum outside diameter of the shaft of the particular state of the class of laparoscope 12 selected for use, which the sheath 14 must accommodate in a smooth, sliding fit. Further, a gap between the outside diameter of the laparoscope shaft and the inside diameter of the sheath 14 must be minimized to avoid the transport and leakage of blood and fluids from the operating field. Still further, minimizing the gap also assures that the laparoscope 12 self-centers in the sheath 14, thereby assuring faithful and accurate visualization through the laparoscope lens.

For example, for a typical laparoscope 12 in the 10 mm class, which measures 0.392 inch, the inside diameter of the sheath 14 is manufactured to 0.405 inch, providing a gap thickness of 0.0064 inch. For a 5 mm laparoscope 12 in the 5 mm class, which measures 0.196 inch, the inside diameter of the sheath 14 is manufactured to 0.218 inch, providing gap thickness of 0.011 inch.

The maximum outside diameter of the sheath 14 for minimally invasive access must take into account the minimum inside diameter of the trocar, which the maximum outside diameter cannot exceed.

For example, for a typical 10 mm trocar that measures 0.509 inch, the outside diameter of the sheath 14 is manufactured to 0.486 inch, providing a gap thickness of 0.0115 inch. For a typical 5 mm trocar that measures 0.324 inch, the outside diameter of the sheath 14 is manufactured to 0.300 inch, providing a gap thickness of 0.012 inch.

It is desirable, given the particular size and configuration constraints of the laparoscopic instrumentation and techniques used, to maximize the outside diameter to the extent possible. This is because, together the inside and outside diameters of the sheath 14 define the wall thickness for the sheath $S_W$. The wall thickness $S_W$, together with the length of the sheath 14, in turn, define the maximum area available for the transport of the CO2 and fluids by the sheath 14. The area of the fluid flow lumen or lumens dedicated to the supply of CO2, in turn, defines the maximum flow rate of the CO2 directed by the deflector assembly 64. The flow rate should be sufficient at a minimum, given the output of the insufflator selected for use, to supply anhydrous CO2 across the lens of the laparoscope 12 sufficient to prevent fogging. Also affecting the effectiveness of the CO2 to defog the lens, is the water content of the anhydrous CO2. Given the same flow rate, the less water that is present in the anhydrous CO2, the greater is the defogging capacity of the assembly. Further, the flow rate desirable should also be sufficient to deflect smoke and surgical debris away from the viewing field of the laparoscopic lens during surgery, so that the anhydrous CO2 directed by the deflector assembly 64 both defogs and deflects debris.

Medical grade CO2 for use with conventional insufflators is typically 99% pure, that is, no more than 1% of the gas is other than CO2, and such medical grade anhydrous CO2 generally has a maximum moisture content of 25 parts per million by volume. Typically, a state of the art insufflator circuit delivers anhydrous CO2 at a max flow rate of about 20 liters per hour. Typically, the insufflator circuit will sense pressure in the circuit and cycle off when the sensed pressure is at or above 15 mmHg and cycle on when the sensed pressure is below 15 mmHg.

Given the above sheath dimensions, and given the supply of typical medical grade anhydrous CO2, a flow rate of at least about 1.0 liters per minute is critical to achieving this objective. Given the above dimensions, and the supply of typical medical grade anhydrous CO2, a flow rate less than 0.8 liters per minute is not sufficient to prevent significant accumulation of moisture on the laparoscope lens.

In a representative embodiment, for a sheath 14 having an inside diameter of 0.405 inch and an outside diameter of 0.486 inch, and a length of 11.25 inch (which accommodates passage of a typical 10 mm laparoscope and its own passage through a conventional trocar) (i.e., $S_W$=0.081 inch), the total area available in the sheath wall is 0.056 square inches. Based upon required structural support within the wall (inside, outside, and radial) the total available area for lumens to transport fluids is 0.027 square inch.

In a representative embodiment, the total lumen area is occupied by five lumens 34 to 42, two for transporting CO2 (34 and 36), one for sterile fluid (38), and two for passive exhaust air venting (40 and 42).

The area of each lumen can be maximized by selection of lumen geometry. In a representative embodiment, lumen geometry is generally triangular or pie shaped with rounded corners. The radial walls that separate the lumens within the sheath 14 are sized to minimize the spacing between the lumens.

In a representative embodiment, CO2 transport is accomplished by two lumens 34 and 36 that extend about 175 degrees about the outer circumference of the sheath 14 and comprising a flow area of 0.013 square inches. Sterile fluid transport is accomplished by one lumen 38 comprising a flow area of 0.003 square inches. Exhaust air venting is accomplished by two lumens 40 and 42 comprising a flow area of 0.011 square inches. The distal openings of the exhaust lumens 40 and 42 desirably are spaced from the distal end of the sheath, to prevent uptake of blood and fluids.

4. Pneumatic Characteristics.

Figure 6:
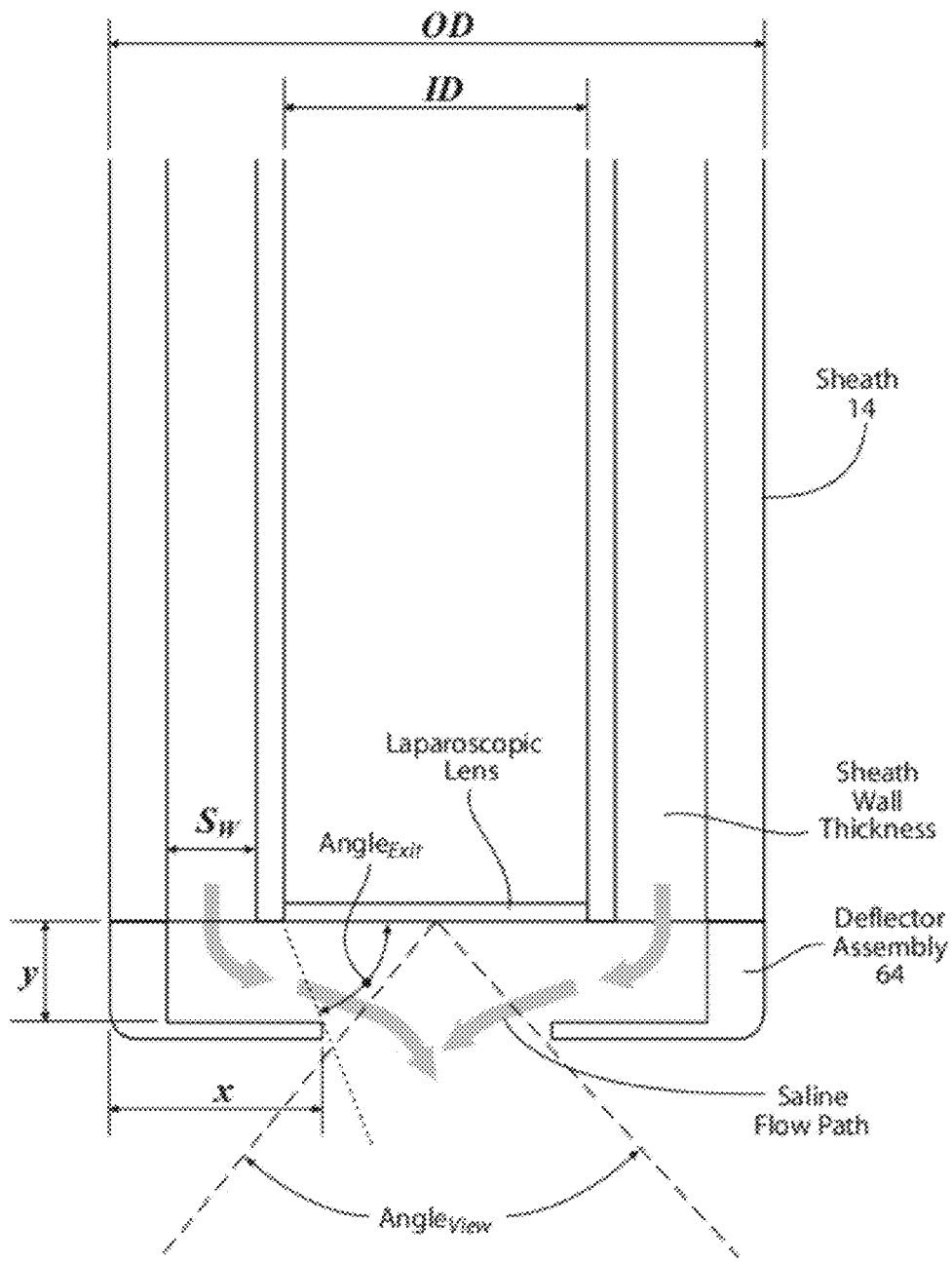
FIG. 6 is a schematic view of the critical physical, pneumatic, and optical characteristics of the deflector assembly shown in FIGS. 5A and 5B.

As diagrammatically shown in FIG. 6, the deflector assembly 64 must overhang the laparoscopic lens by a prescribed transverse distance, defining a deflection width X, sufficient to change the direction of CO2 flowing axially through lumens of the sheath 14 (i.e., along the axis of the laparoscope shaft) into a non-axially, transverse path across the laparoscopic lens (i.e., at an angle relative to the axis of the laparoscope shaft). Still, the distance of the deflection width X should not extend to the point that is obstructs the field of the view of the laparoscopic lens. This is an example where a pneumatic characteristic of the deflector assembly 64 overlaps with an optical characteristic. Further optical characteristics will be described in greater detail below.

The deflector assembly 64 must also project axially beyond the distal terminus of the sheath 14 by a prescribed axial distance, defining an air channel distance Y, sufficient to maintain the CO2 flowing along the path bounded by the deflection width X at a distance sufficiently close (proximal) to the laparoscopic lens to achieve the desired shear flow effect, but without forming an abrupt flow bend that can lead to a reduction in the desired CO2 flow velocity.

Together, the deflection width X and the channel distance Y define the pneumatic characteristics of the deflection assembly. At the desired minimum flow rate, the pneumatic characteristics create a flow path that conveys CO2 continuously across the laparoscopic lens at the desired flow velocity, in shorthand called the "wind shear." The pneumatic characteristics of the CO2 "wind shear" across the laparoscopic lens prevent fogging, as well as desirably deflect smoke and surgical debris away from the viewing field of the laparoscopic lens during surgery.

Together, the pneumatic characteristics defined by the deflection width X and the channel distance Y create an exit angle $A_{EXIT}$, measured between the plane of the laparoscopic lens and the terminal edge of the deflector assembly 64. The exit angle $A_{EXIT}$ must be less than a maximum angle of 45 degrees, else the flow path of the CO2 will not pass sufficiently both across and proximal to the laparoscopic lens. To maintain a desired exit angle $A_{EXIT}$, the channel distance Y should be at least equal to the wall thickness of the sheath $S_W$ and should not exceed 1.5 times the wall thickness of the sheath $S_W$. The deflection width X should be at least equally to two times the channel distance Y, but not extend into the field of view of the laparoscopic lens.

5. Optical Characteristics

The optical characteristics of the deflector assembly 64 are selected (i) to not block or reduce the illuminated image of the operating field provided by the laparoscope 12; (ii) not decrease the intensity of the illumination provided by the laparoscope 12 on the operating field; and (iii) prevent reflection of illumination light at the lens of the laparoscope 12.

As discussed above, the maximum deflection width X takes into account one of the desirable optical characteristics; namely, the deflection width X should not obstruct the field of the view of the laparoscopic lens.

To prevent the decrease of the illumination, the deflector assembly 64 is desirably made from a material having high light transmission properties (i.e., transparency), to not interfere with the passage of light through the light cable 30 onto the operating field as well as the passage of the reflected image conveyed to the camera cable 32 of the laparoscope 12.

Furthermore, the material and surface finish of the deflector assembly 64 must pose minimal reflectively to light. In a representative embodiment, the deflector assembly 64 is made from Bayer Makrolen Rx1805 with a surface finish defined as SPI/SPE A-3.

6. Orientation

As before described, CO2 transport is accomplished by two lumens 34 and 36 that extend about 175 degrees about the outer circumference of the sheath 14. For a 0° shaft tip (see FIG. 5A), the orientation of the deflector assembly 64 relative to the laparoscopic lens is not critical. However, for angled shafts (e.g., 30° shaft tips and 45° shaft tips) (see FIG. 5B), the orientation of the deflector assembly 64 relative to the laparoscopic lens is critical.

As FIG. 5B shows, the angled tip of a typical laparoscope 12 has a high end 66 and a low end 68. The lens slopes at the prescribed angle between the high end 66 and the low end 68. In a laparoscope 12 having a angled tip, the illumination cable 30 (transmitting light onto the operating field) is located at the high end 66 of the angled tip, and the camera cable 32 (transmitting reflected light back to the camera) is located at the low end 68 of the angled tip. To provide the desired wind shear effect on an angled tip, it is critical that the deflector assembly 64 be oriented relative to the sloped laparoscopic lens such that the flow CO2 is directed across the sloped plane of the lens from the low end 68 of the tip toward the high end 66 of the tip. In this arrangement, the defogging and debris deflection flow path originates proximal to the camera cable 32, which effectively comprises the eyes of the OR team. In this arrangement, the desired exit angle $A_{EXIT}$ directs the flow path of the CO2 both sufficiently across and proximal to the sloped plane of the laparoscopic lens to achieve optimal defogging and debris deflection.

F. Sterile Fluid Flush

As previously explained, if desired, the tubing set 16 can also include, connected to the quick exchange coupler 22, a length of tubing 70 sized and configured for connection to a source 72 of sterile fluid, such as saline or sterile water (as shown in FIGS. 1A and 2A). Preferably, the sterile fluid includes in solution a "surface-active agent" that stabilizes mixtures of oil and water (e.g., fat) by reducing the surface tension at the interface between the oil and water molecules.

The quick exchange coupling 20 on the manifold 18 (see FIG. 3A/3B and 4A/4B) can also include a port to integrally connect the sterile fluid tubing 70 to direct the sterile fluid through the separate lumen 38 in the sheath 14 to the distal end of the sheath 14. The deflector assembly 64 directs the sterile fluid across the laparoscopic lens.

As shown in FIGS. 1A/2A, the sterile fluid tubing 70, if present, desirably includes an in-line pumping device 72. The in-line pumping device 72 is sized and configured to be operated on demand by a person at the OR table to convey bursts of sterile fluid through the manifold 18 through the lumen to the distal end of the sheath 14. The in-line pumping device 72 and source can be integrated and comprise, e.g., a 20 cc syringe filled with sterile fluid and connected by a tubing luer-lock on the saline tubing. Alternatively, the in-line pumping device 72 and source can be separate and comprise, e.g., a bag of sterile fluid, a spike connection on the saline tubing of the tubing set 16 to open communication with the bag in conventional fashion, and an inline squeeze bulb or the like to pump burst of sterile fluid from the bag to the quick exchange coupler 22.

In this arrangement, the deflector assembly 64 is also sized and configured to direct the burst of sterile fluid in a desired path across the laparoscopic lens. The bursts of sterile fluid serve to flush debris off the end of the lens that may eventually accumulate, thereby cleaning the lens. Thereafter, bursts of air supplied through the deflector assembly 64 by a squeeze pump 74 in the tubing set 16 (see FIGS. 1A/2A) serve to clear residual fluid droplets off the lens and away from the deflector assembly 64 to maintain the desired flow path and flow velocity of $CO_2$ established by the deflector assembly 64 continuously across the laparoscopic lens, to maintain an acceptable view.

In an illustrative embodiment (see FIGS. 5A and 5B), the deflector assembly 64 directs the bursts of sterile fluid or air along a plurality of individual diverging channels 76 (three are shown). The diverging channels 76 distribute the bursts of sterile fluid or air in a fanning pattern across the lens of the laparoscope 12. In the illustrative embodiment, the diverging channels 76 discharge the bursts of sterile fluid or air in a path that is generally ninety-degrees to the path of $CO_2$. This orientation of the sterile fluid path relative to the $CO_2$ path across the lens, optimal for effective lens cleaning, applies to both 0° shaft tips and angled tips (e.g., 30° shaft tips and 45° shaft tips).

II. Use of the View Optimizing Assembly

The view optimizing assembly is well suited for use as a single-use disposable laparoscopic accessory device to facilitate intra-operative defogging and debris deflection (due to the flow of anhydrous $CO_2$) and cleaning of the lens of a laparoscope 12 (due to burst of sterile fluid, preferably including a "surface-active agent") during minimally invasive surgery, while also maintaining visualization of the surgical site.

FIGS. 7 to 34 illustrate a representative method including the set up and use of the view optimizing assembly using sterile technique by qualified technicians/operating room personnel.

The procedure can be incorporated into written instructions for use that accompany the packaging. The instructions can also be supplied separately, e.g., embodied in separate instruction manuals, or in video or audio tapes, CD's, and DVD's. The instructions for use can also be available through an internet web page.

The instructions can direct the OR set-up to peel open the outer pouches in which the components of the view optimizing assembly (shown in FIG. 7), and remove the sterile contents on the sterile field. The sheath 14/manifold 18 assembly is removed, taking care to prevent damage to the walls of the sheath 14 or to its distal end, and also keeping the tubing set 16 and vent device 24 on the sterile field prior to making necessary connections.

During set up (see FIGS. 8 and 9), the sheath 14 (with the manifold 18, which is integrally connected to the sheath 14 during manufacture, called a sheath assembly) can be assembled to the corresponding laparoscope 12. In this representative example, it is contemplated that the OR team plan to use a 0-degree laparoscope 12 (see FIGS. 8 and 9) and at least one angled laparoscope 12 (see FIGS. 10 and 11), e.g., a 30-degree and/or a 45-degree laparoscope 12. Therefore, during set-up, a sheath assembly for each laparoscope 12 selected for use will be pre-assembled to the corresponding laparoscope 12.

Figure 8:
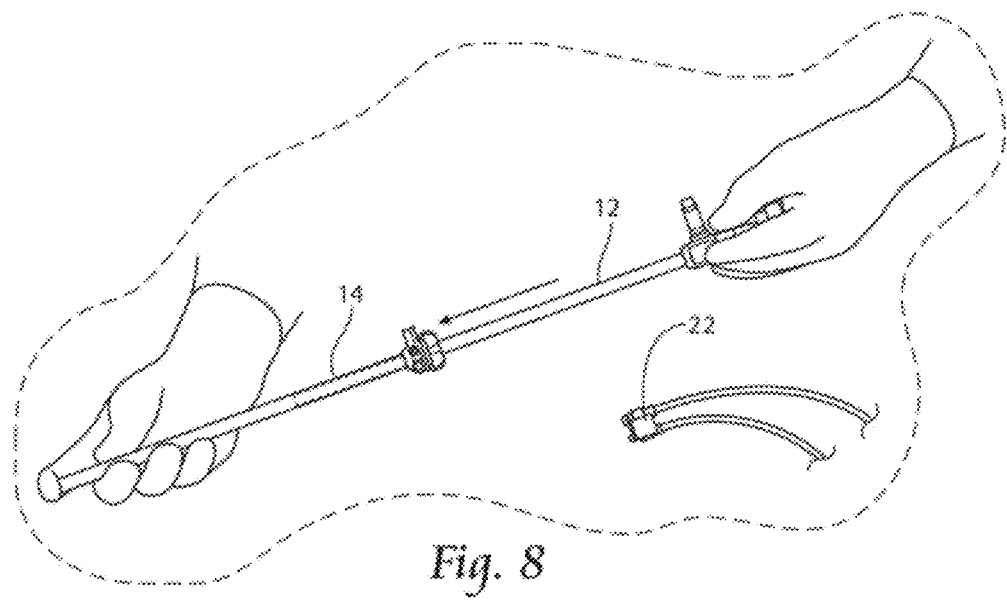
Figure 9:
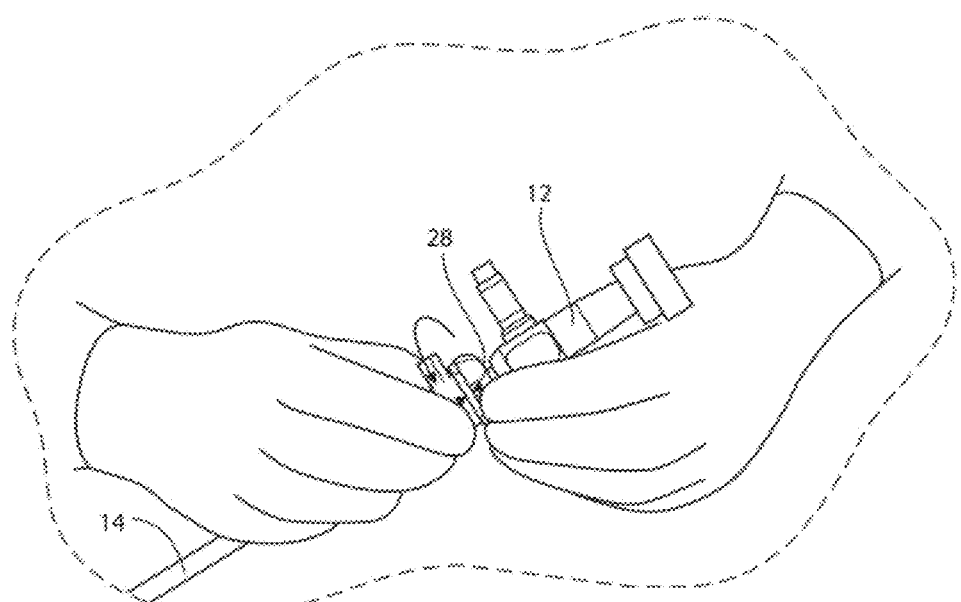
Figure 10:
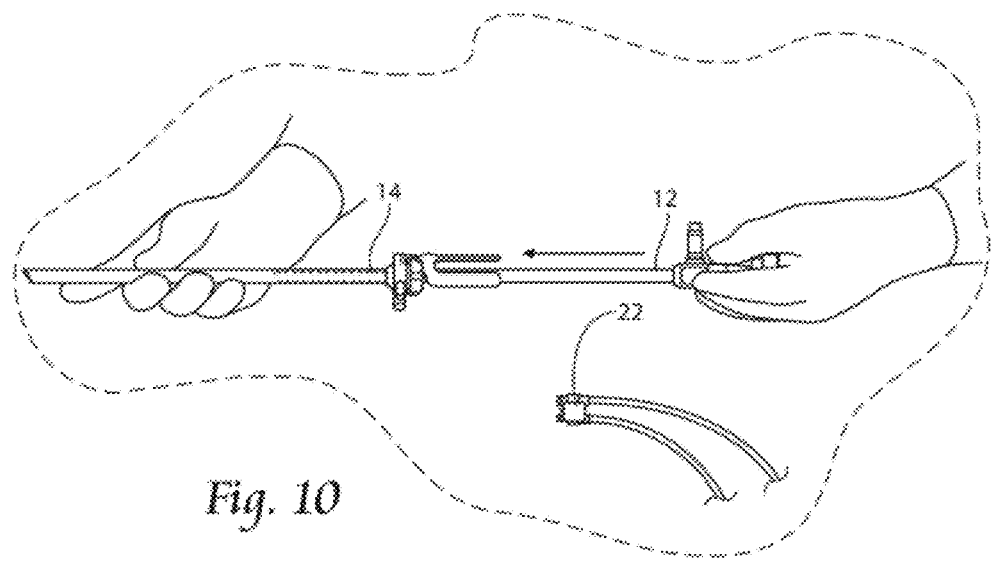
Figure 11:
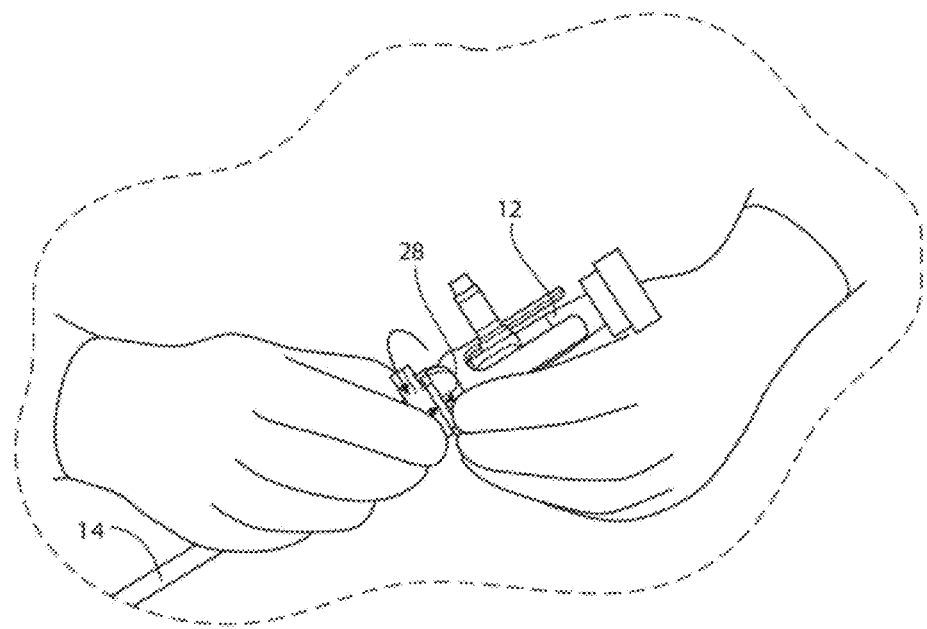

As FIGS. 8 and 10 show, while gently pressing the tip of the sheath assembly against one hand or finger-tip, the laparoscope 12 can be inserted down into the sheath 14. The sheath 14 is sized and configured so that the laparoscope 12 will slide smoothly through the sheath 14. Insertion continues until the lens and distal rim of the laparoscope 12 seat against the stop at the distal end of the sheath 14. The laparoscope 12 will "bottom out" inside the sheath 14 against the stop 26, assuring correct axial alignment of the lens with the deflector assembly 64.

If the laparoscope 12 is angled (as shown in FIG. 10), the corresponding sheath assembly will also include an alignment fork guide 78. The light post of the scope seats within the alignment fork guide 78, therefore assuring correct rotational alignment between the angled lens and the deflector assembly 64.

The laparoscope 12 (now fully inserted into the sheath 14) the manifold 18 are supported by hand, a member of the OR set-up team rotates the locking collar 28 on the sheath assembly in the desired direction, e.g., clockwise (see FIGS. 9 and 11), indicated by an arrow on the locking collar 28, until a firm stop is felt tactilely (e.g., after approximately one-third (⅓) of a turn). Registration of an alignment mark on the locking collar 28 and an alignment mark on the manifold 18 serves to visually confirm that the laparoscope 12 is secured against axial movement relative to the sheath 14.

The insufflator is set up off the sterile field. Once the patient is draped on the sterile field, and it is expected that the end of the output tubing from the insufflator (originating from the insufflator off the sterile field) will brought onto the sterile field. It is also expected that the light cable 30 and the camera cable 32 for the laparoscope 12 will be brought onto the sterile field.

Figure 12:
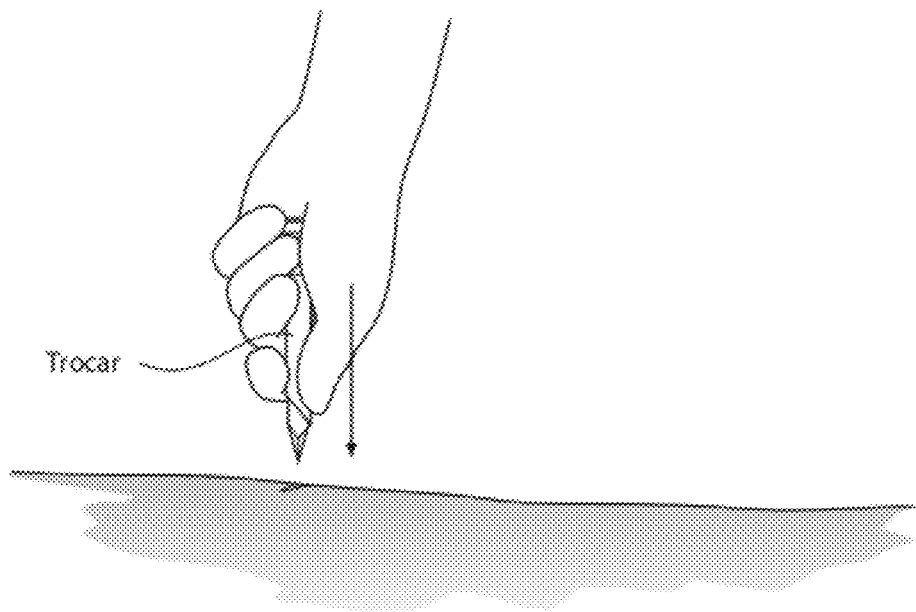
Figure 13:
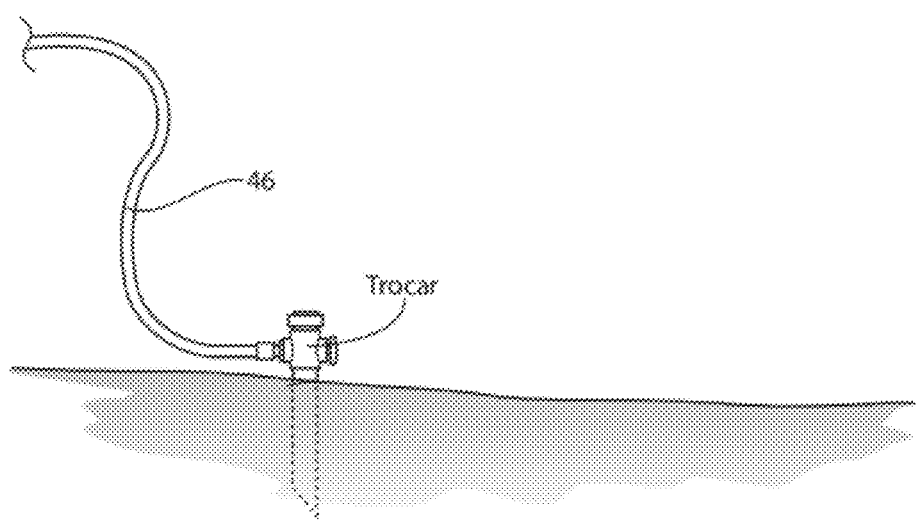

As FIGS. 12 and 13 generally show, the OR team makes an incision to gain access to the laparoscopic operating site within the body, e.g., into the abdominal cavity through the abdominal wall. A first trocar with a stopcock valve (which may take the form of an optical trocar) is inserted through the incision. Alternatively, according to physician preference, the first trocar can be pushed through abdominal wall with only a skin incision. The obturator (the sharp inner insert of the trocar) is removed from the first trocar once it is in position.

The insufflator line of the tubing set 16 on the sterile field is connected to the output tubing of the insufflator circuit on the sterile field. The first branch 46 of the tubing set 16 on the sterile field, originating at the Y-connector 44, is coupled to the stopcock valve of the first trocar (see FIG. 13). The stopcock valve is opened, and the insufflator is turned on. $CO_2$ output of the insufflation circuit inflates the abdomen through the first trocar.

During this time (see FIGS. 8 and 10), the second branch 48 of the tubing set 16 on the sterile field, also originating at the Y-connector 44, and the quick exchange coupler 22 integrally attached to it can remain on the sterile field in a free, unconnected condition as the insufflator supplies $CO_2$ through the first branch 46. The one-way check valve in the quick exchange coupler 22 serves to block flow of $CO_2$ through the second branch 48, even as the insufflator supplies $CO_2$ through the first branch 46. The entire $CO_2$ pressure of the insufflator circuit is, at the present, delivered to the first trocar through the first branch 46.

The first laparoscope 12 selected for use, which has been pre-inserted into the sheath 14 by the OR set-up team as just described, is handed to personnel at the OR table at the appropriate time. On the sterile field, personnel at the OR table connect the light cable 30 and the camera cable 32 to the laparoscope 12 (see FIG. 14). On the sterile field, personnel at the OR table now connect the quick exchange coupler 22 of the tubing set 16 to the quick exchange coupling 20 of the manifold 18 (see FIG. 15). The one way valve opens, and a small portion of the output of the insufflator circuit is routed by the second branch 48 through the manifold 18 into to the sheath 14.

The laparoscope/sheath assembly is then placed as an integrated unit through the first trocar to get an initial view of the abdominal cavity (see FIG. 16). Due to the technical features of the deflector assembly 64, $CO_2$ flows over the lens, eliminating fogging and also deflecting away debris. If present, the pump (e.g., the cc syringe) filled with sterile fluid (preferably with a "surface-active agent") and connected to the tubing luer-lock, can be operated by personnel at the OR table to flush sterile fluid through the deflector assembly 64 of the sheath 14. The deflector assembly 64 directs the fluid bursts across the lens in a path generally 90-degrees offset from the $CO_2$ path. Once this is done, the bulb on the tubing set 16 can be pumped several times introduce bursts of air to clear droplets off the lens and away from the tip deflector, to maintain to the continuous directed flow of $CO_2$ across the laparoscopic lens.

Figure 17:
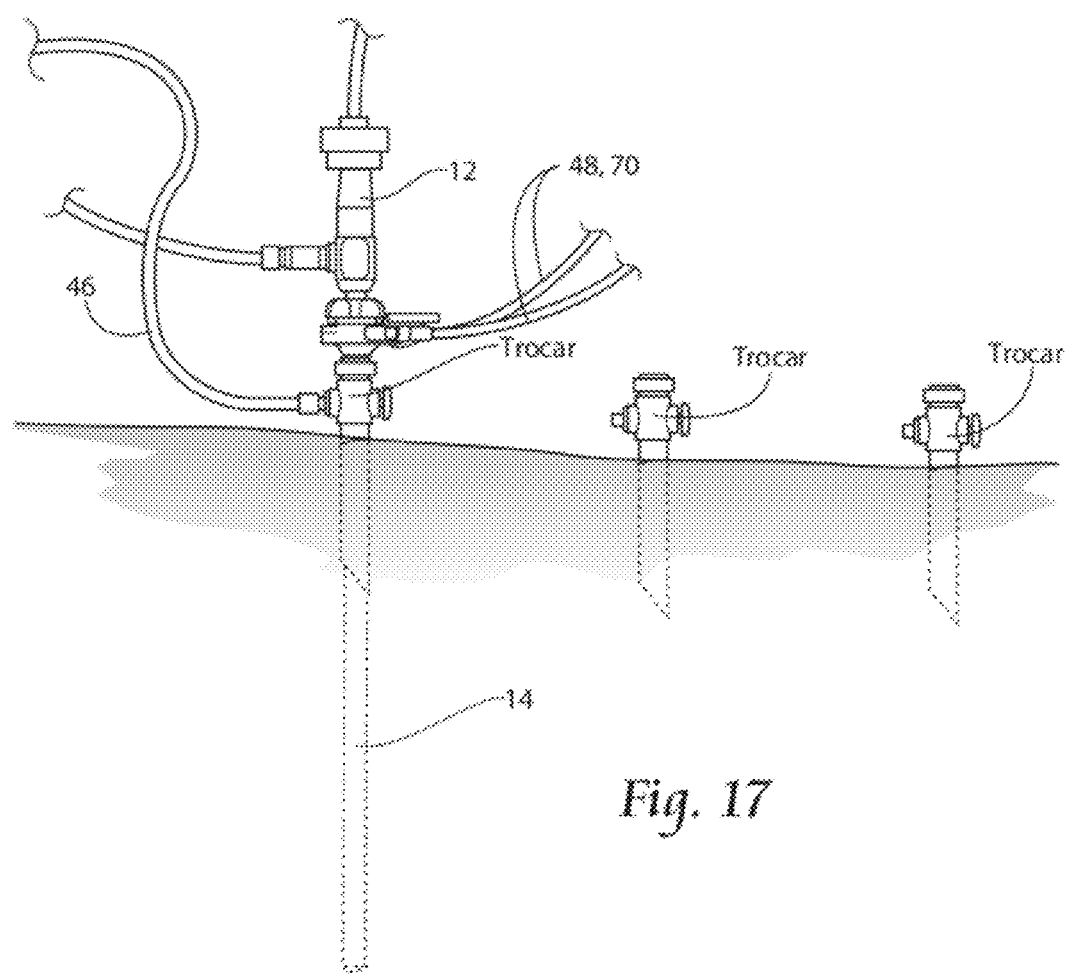
Figure 18:
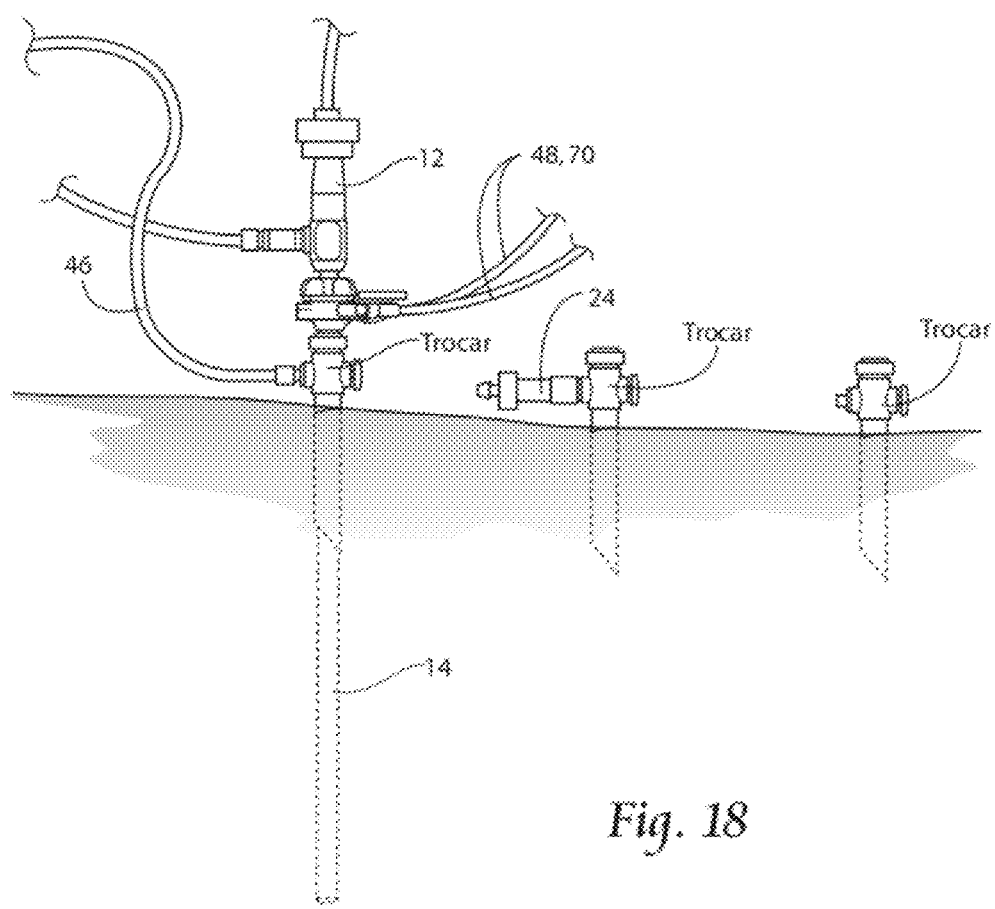

Once a satisfactory view is achieved, additional ancillary trocars with stopcock valves, e.g. three to four, or more, are also placed through incisions to provide access for other instruments (see FIG. 17). The trocar vent device 24 provided with the view optimizing assembly is desirably placed in the stopcock of one of the ancillary trocars, and the stopcock valve is opened (see FIG. 18).

Figure 19:
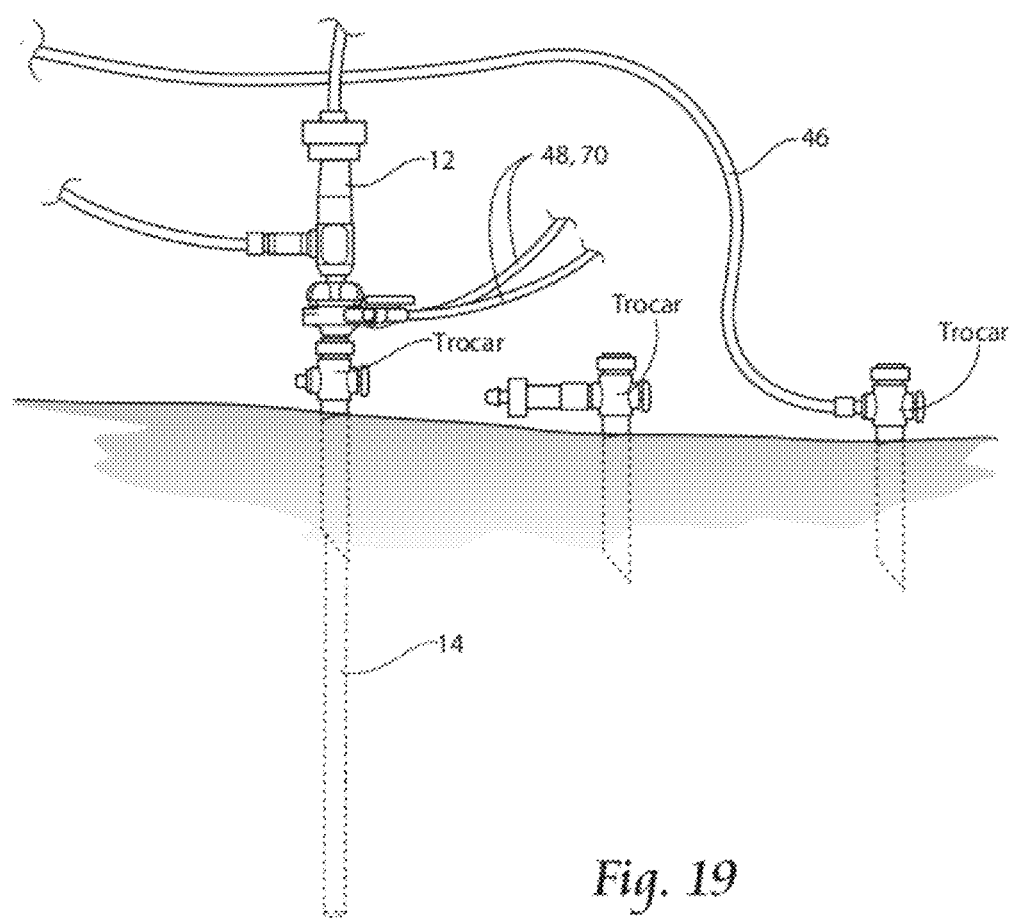
Figure 20:
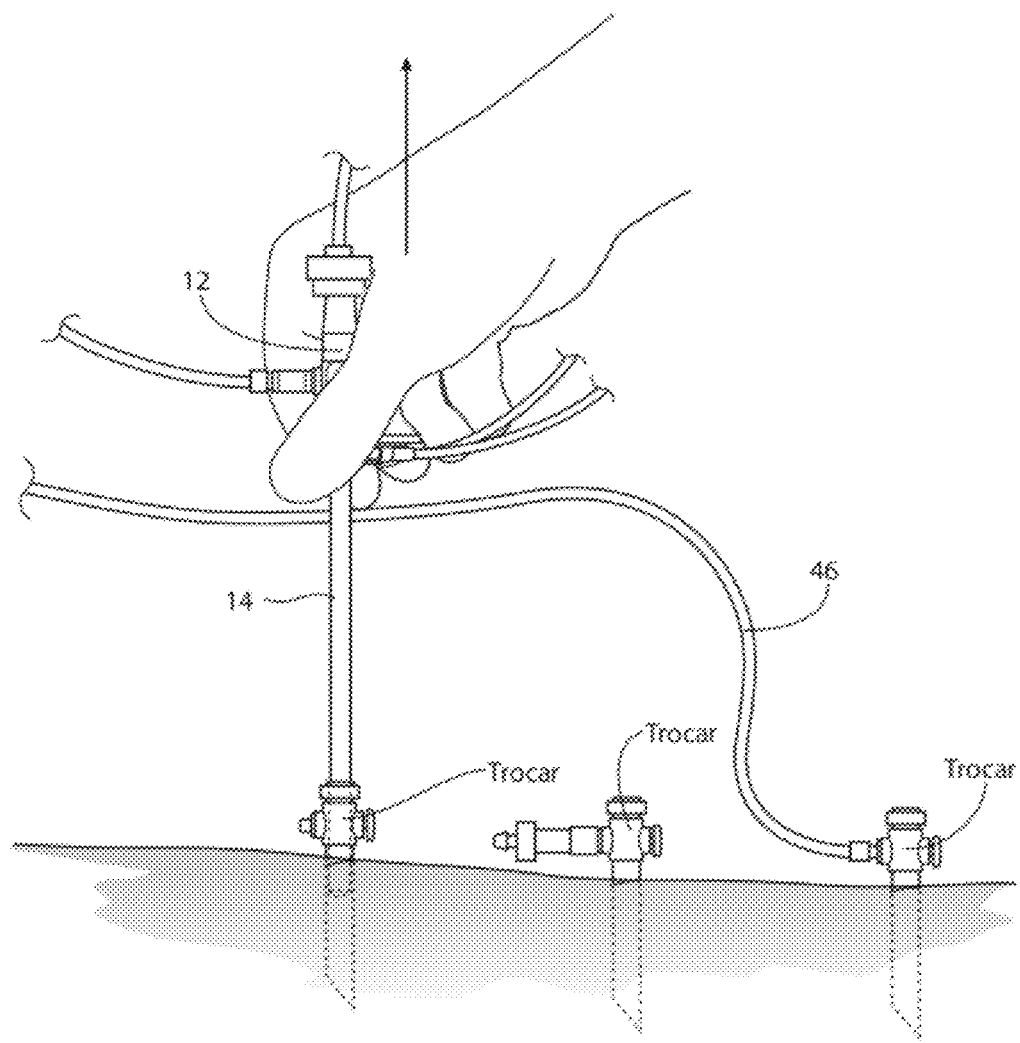
Figure 21:
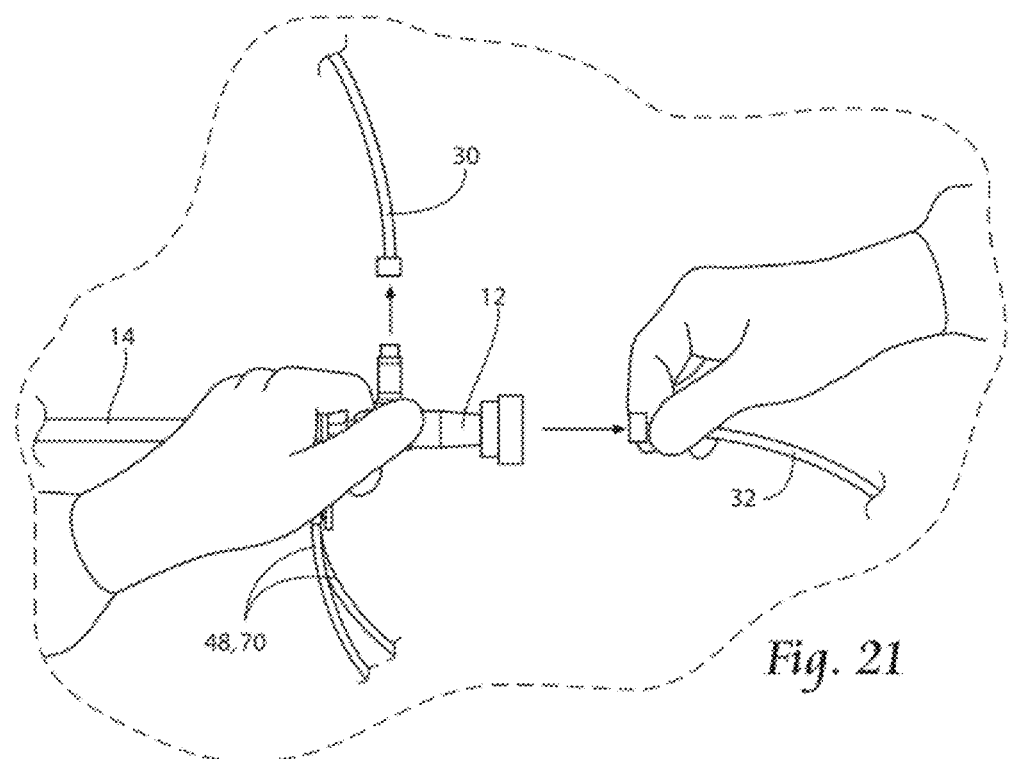

As FIG. 19 shows, a member of the OR team preferable decouples the main insufflation line (the first branch 46 tubing of the Y-connector 44 of the tubing set 16) from the first trocar to the stopcock valve of another available trocar on the sterile field (except the trocar to which the vent device 24 is coupled). This other trocar then serves as the main insufflation trocar, separate from the first trocar, which now serves as the main visualization trocar. In this way, the main $CO_2$ insufflation provided for the duration of the surgery is provided by an insufflation trocar that is also not the visualization trocar. The controlled leak of insufflation pressure that the vent device 24 provides creates a pressure gradient within the pneumo-peritoneum that helps maintain a generally continuous flow of $CO_2$ from the deflector assembly 64 across the lens, despite periodic cycling of the insufflator. Lumens 40 and 42 in the sheath 14 (previously described) can also serve as additional passive vents, to leak insufflation pressure out through the manifold 18.

The surgery proceeds. The deflector assembly 64 provides intra-operative defogging and cleaning of the laparoscope lens during the minimally invasive surgery, while maintaining visualization of the surgical site. The sterile fluid flush mechanism can be used, as desired, if required to augment visualization by flushing the lens. If this is done, the bulb on the tubing set 16 should be pumped several times to clear droplets off the lens and away from the deflector assembly 64 to maintain the $CO_2$ curtain across the lens.

During the surgery, the OR team can decide, e.g., that one portion of the procedure is better visualized with a different angle scope. The quick exchange features of the coupler of the tubing set 16 and the coupling of the manifold 18, greatly facilitate the exchange of one laparoscope 12 for another with minimal interruption of the surgical procedure and without compromising the sterile field.

To exchange one laparoscope 12 for another, a member of the OR team withdraws the laparoscope/sheath assembly an integrated unit from the visualization trocar (see FIG. 20).). A member of the OR team disconnects the laparoscope 12 from the light cable 30 and camera cable 32 (see FIG. 21). A member of the OR team uncouples the quick exchange coupler 22 from the quick exchange coupling 20, freeing the laparoscope/sheath assembly from the tubing set 16 (see FIG. 22). The disconnected laparoscope/sheath assembly is handed as an integrated unit to a member of the OR team, e.g., a scrub nurse (see FIG. 23). There is no reason to remove the sheath 14 from the matching laparoscope 12 at this time. This can be accomplished later, after the surgery is all done.

The laparoscope/sheath assembly that includes the second laparoscope 12 that is to be used, has already been assembled into an integrated unit, as previously described. This pre-assembled unit is handed to a member of the OR team (see FIG. 24). A member of the OR team connects the second laparoscope 12 to the light cable 30 and camera cable 32 (see FIG. 25). A member of the OR team couples the quick exchange coupler 22 of the tubing set 16 to the quick exchange coupling 20, connecting the second laparoscope/sheath assembly in flow communication with the tubing set 16 (see FIG. 26), completing the quick exchange. The second laparoscope/sheath assembly is inserted into the visualization trocar (see FIG. 27).

The quick connect feature functions with a manifold 18 associated with every sheath 14. The tubing set 16 on the sterile field can be rapidly disconnected, but need not, and desirably is not, exchanged with another tubing set 16. During a given surgical procedure, the same tubing set 16 serves every laparoscope/sheath assembly used (unneeded tubing sets 16 that came with the additional sheaths can be simply discarded).

The surgery proceeds using the second laparoscope/sheath assembly.

Additional quick exchanges of laparoscopes can be accomplished as surgery proceeds in the manner just described.

Figure 28:
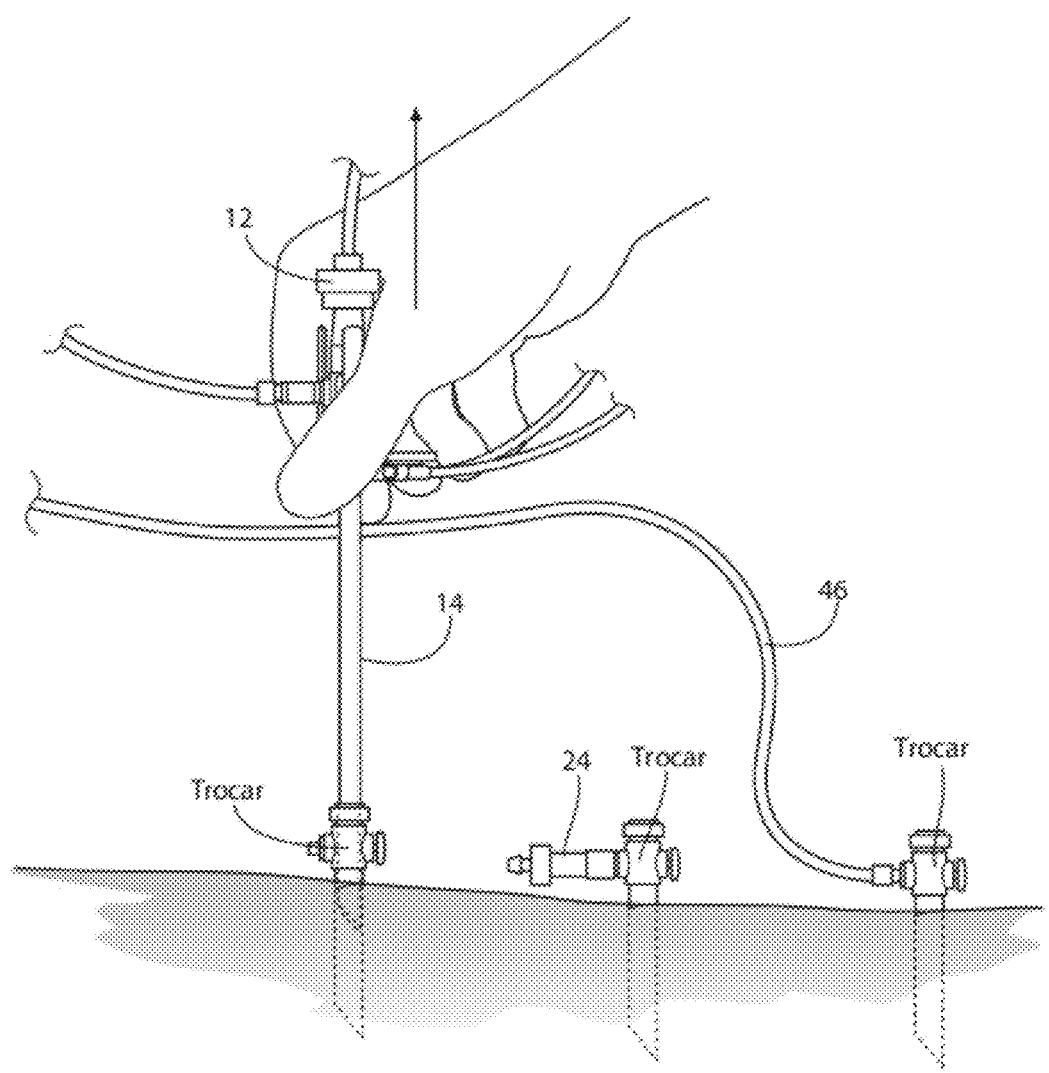
Figure 29:
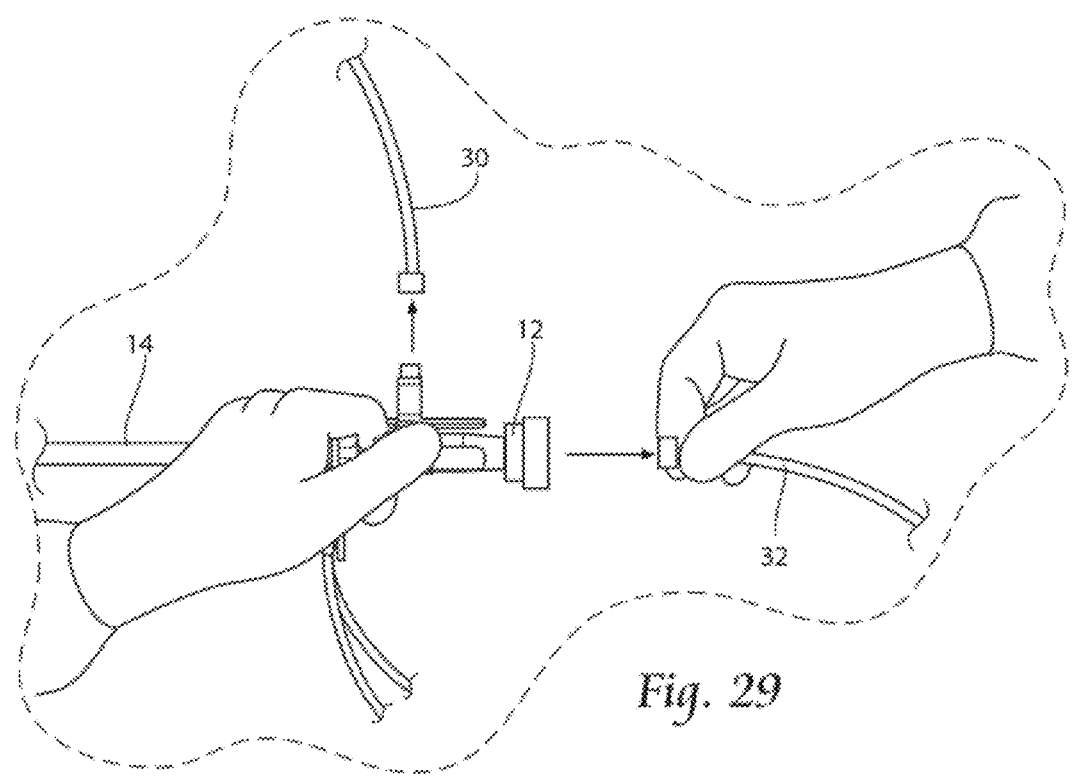
Figure 30:
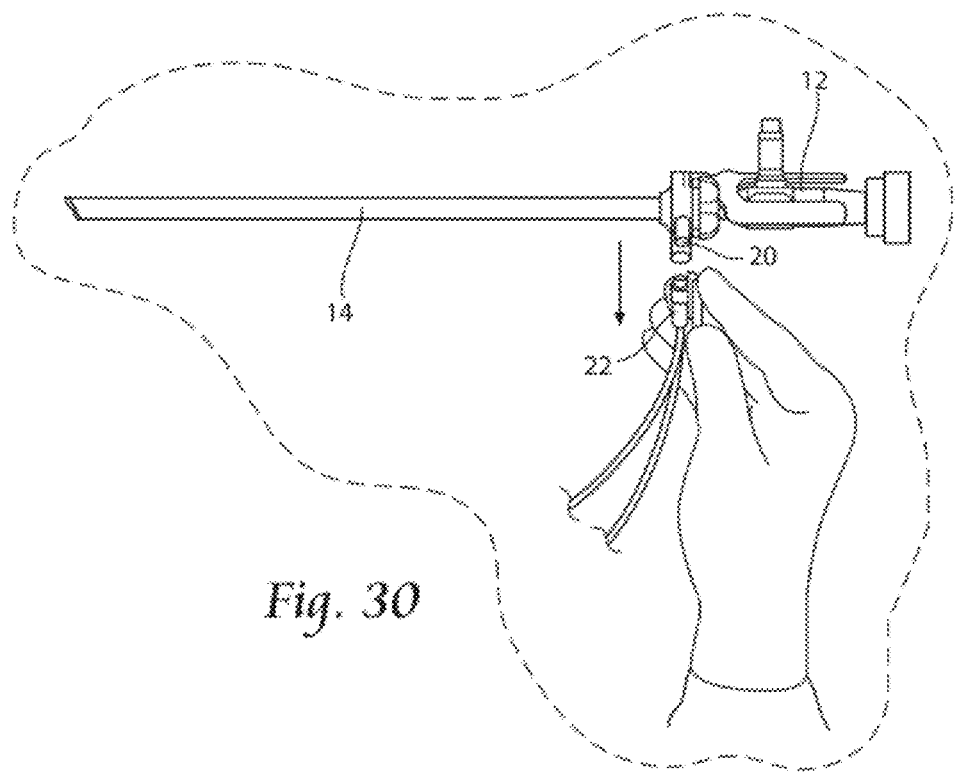
Figure 31:
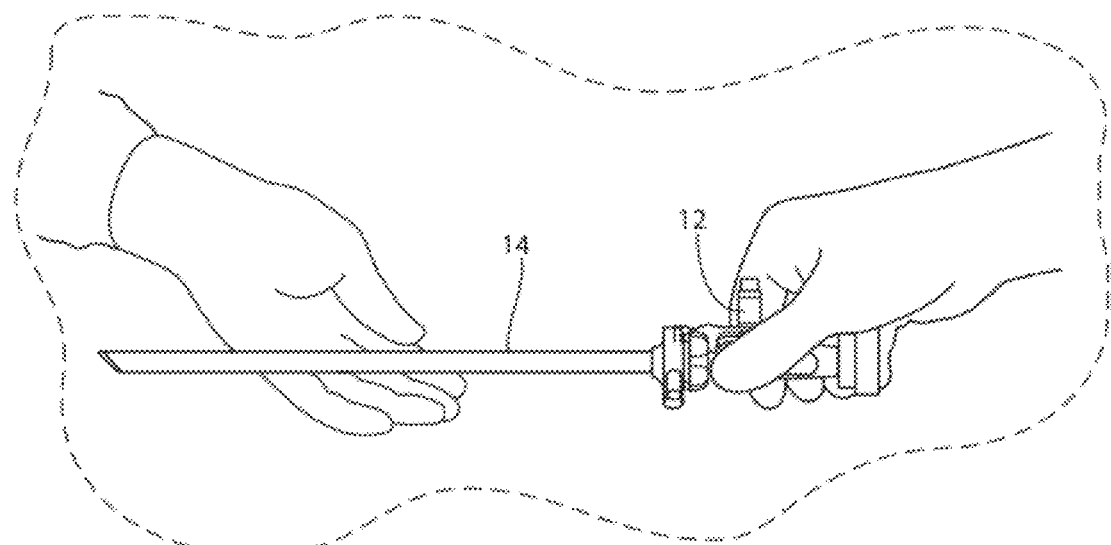
Figure 32:
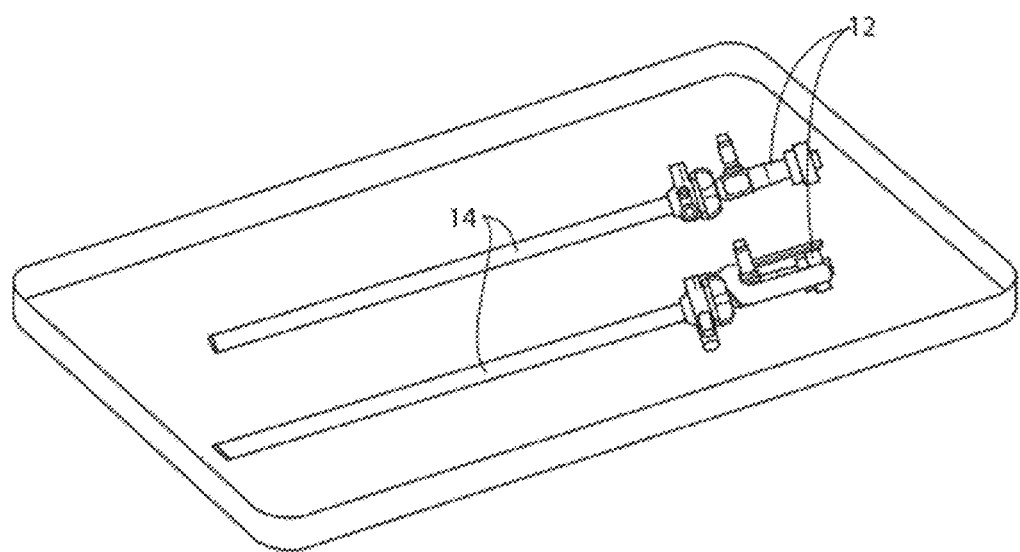

Once surgery is completed, all instruments, including the laparoscope/sheath assembly in use are removed from the visualization trocar (see FIG. 28). A member of the OR team disconnects the laparoscope 12 from the light cable 30 and camera cable 32 (see FIG. 29). A member of the OR team uncouples the quick exchange coupler 22 from the quick exchange coupling 20, freeing the laparoscope/sheath assembly from the tubing set 16. The laparoscope/sheath assembly is handed to a member of the OR team (see FIG. 31), and placed alongside previously used laparoscope/sheath assemblies (see FIG. 32).

Figure 33:
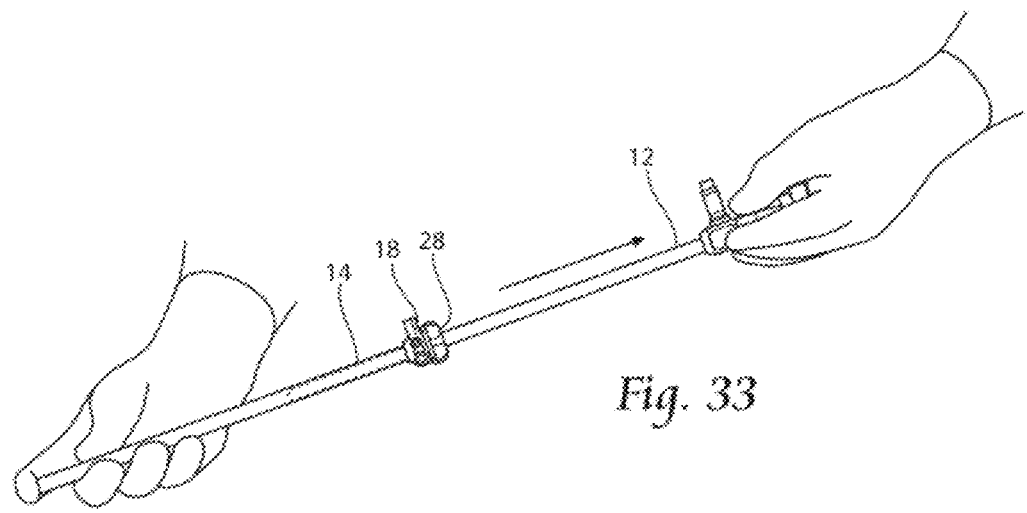
Figure 34:
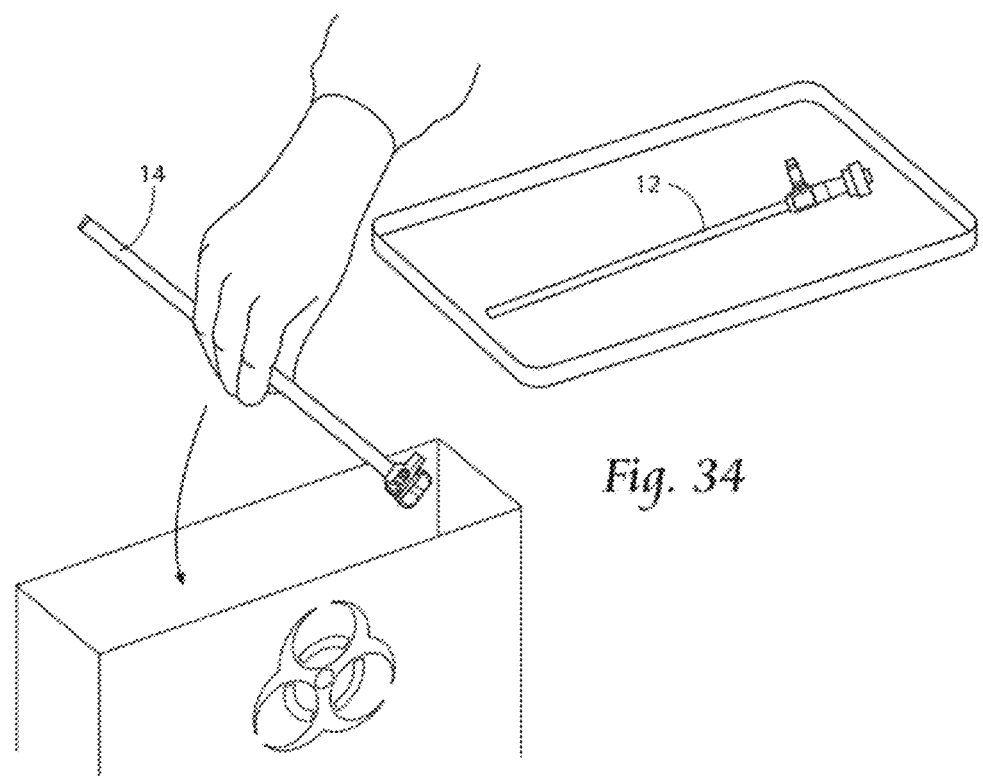

Access sites are closed. The insufflator is shut off. The tubing set 16 is disconnected from the insufflator circuit. The lock collars on the manifolds 18 are loosened, and laparoscopes are withdrawn from the sheaths for reuse (FIG. 33). The sheaths and tubing set 16 are disposed of (FIG. 34).

Some trocars are called "optical trocars" that have a lumen within the obturator, that is within the trocar. If the lens of a laparoscope 12 is first placed into the center of an optical trocar to guide the first trocar insertion, then the sheath 14 cannot be present on the laparoscope 12, as the combination cannot fit through the lumen of the obturator. In this situation, the laparoscope 12 is used without a sheath 14 is used to place the first trocar. The laparoscope 12 is then inserted through the sheath 14, and connection of the tubing set 16 occurs in the manner just described. With the obturator removed from the trocar, the laparoscope/sheath assembly is placed through the first trocar in the manner described.

III. Self-Contained Supply and Processing of Air for the Deflector Assembly

Figures 35A, 35B:
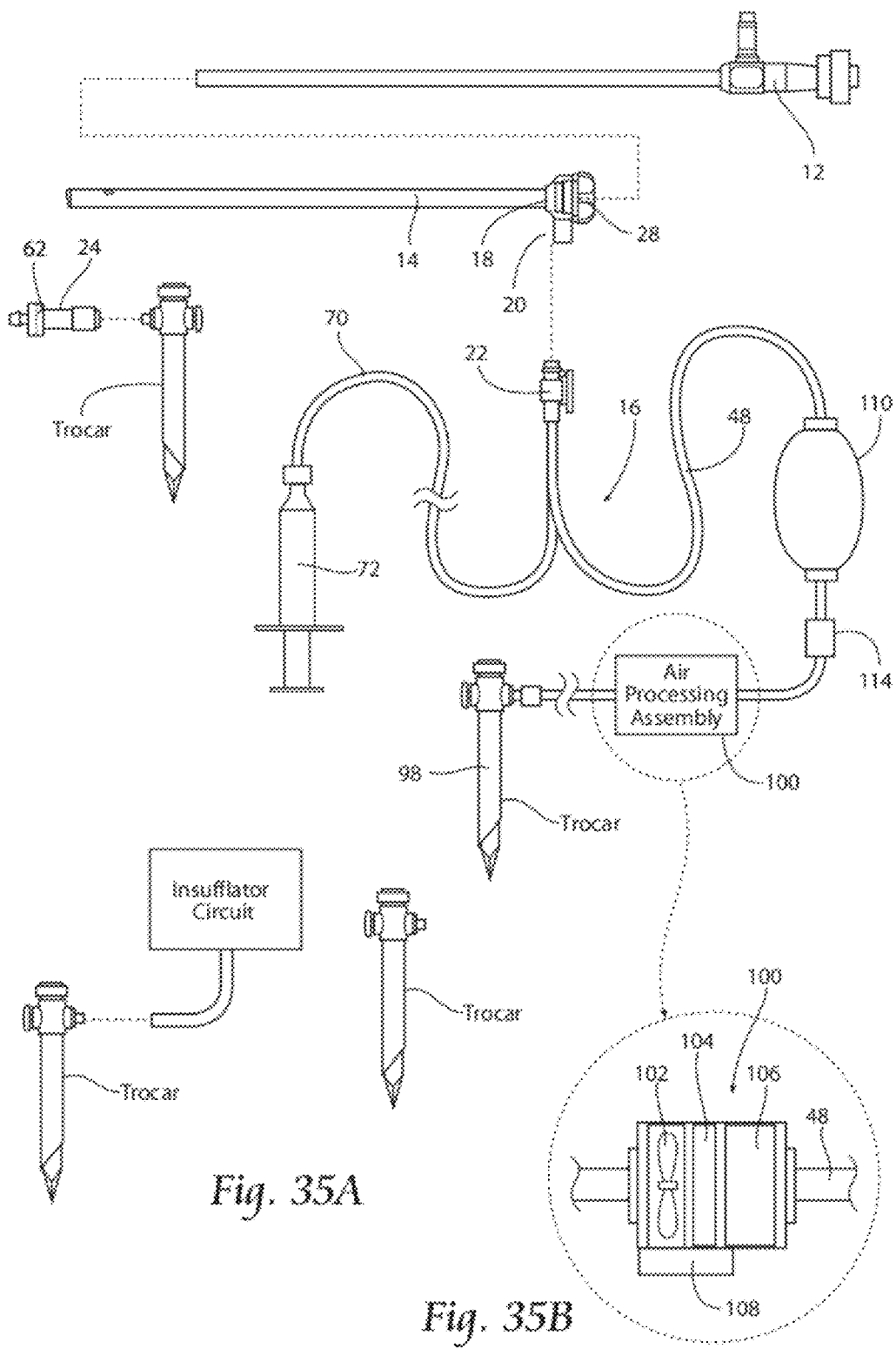
FIG. 35A shows a view optimizing assembly for use with a laparoscope having a tubing set with an in-line air processing or conveying assembly.
FIG. 35B is an enlarged section view of the air processing or conveying assembly shown in FIG. 35A.

FIG. 35A shows a view optimizing assembly 10 for use in association with a state of the art laparoscope 12, like that shown in FIGS. 1A/1B (blunt tip) and FIG. 2A/2B (angle shaft tip). In many respects, the assembly 10 shown in FIG. 35A includes components like that shown in FIGS. 1A/1B and 2A/2B, and common reference numbers are likewise assigned to these common components.

As shown in FIG. 35A, the view optimization assembly 10 includes a sheath 14 and a manifold 18 that is assembled to the sheath 14 and that includes a quick exchange coupling 20; a tubing set 16 which includes a quick exchange coupler 22 that mates with the quick exchange coupling 20 on the manifold 18; and (optionally) a vent device 24. The sheath 14 is sized and configured to receive a laparoscope 12 having a prescribed tip angle, length, and diameter.

In FIGS. 1A/1B and 2A/2B, the tubing set 16 includes lengths of flexible medical grade tubing with a coupler 44 that connected to an existing CO2 insufflation circuit. As previously described, in this arrangement, the deflector assembly 64 is sized and configured to direct the small portion of the CO2 from the insufflation circuit in a prescribed flow path and flow velocity across the laparoscopic lens. In this arrangement, as previously explained, a second branch 48 of the tubing set 16 diverts a small portion of the CO2 output (e.g., 20% or less) of the insufflation circuit to the quick exchange coupler 22. When coupled to the manifold 18, the diverted portion of the CO2 output is conveyed through lumens in the sheath 14 to a deflector assembly 64 at the distal end of the sheath 14 (see FIGS. 5A(1) and 5A(2) for a blunt shaft tip and FIGS. 5B(1) and 5B(2) for an angled shaft tip). As previously described, conventional insufflators are adapted to cycle on and off to maintain a preset and suitable pressure within the patient's body cavity. Therefore, when the insufflation circuit is cycled off, the diverted portion of the CO2 output conveyed to the deflector assembly 64 is interrupted.

The embodiment shown in FIG. 35A differs from the previously described embodiment in that the second branch 48 of the tubing set 16 is not coupled to the insufflation circuit. Rather, the tubing set 16 is coupled to a separate, dedicated air supply trocar 98 (with stop cock valve). The trocar 98 is placed through an incision, and when the stop cock valve is opened, provides communication with the insufflated CO2 environment present in the operating cavity. With the obturator removed, the trocar 98 may also serve to provide additional access for an instrument into the operating cavity.

In this arrangement, the second branch 48 includes an in-line air processing or conveying assembly 100 (see also FIG. 35b) contained within a housing coupled in air flow communication with the tubing of the second branch 48. The in-line air processing or conveying assembly 100 serves to draw air from the insufflated CO2 environment present in the operating cavity through the trocar 98, for delivery by the sheath 14 continuously through the deflector assembly 64, independent of operation of the insufflation circuit itself. Even when the insufflation circuit is cycled off, the air processing or conveying assembly 100 operates to draw air from the insufflated CO2 environment present in the operating cavity, to the deflector assembly 64 of the sheath 14. Further, the in-line air processing or conveying assembly 100 can also serve to beneficially process or treat the air drawn from the insufflated CO2 environment present in the operating cavity, after it is removed from the operating cavity and before it is conducted by the deflector assembly 64, to remove, e.g., smoke, particulates, aerosolized pathogens, and water vapor from the airflow before it is conducted by deflector assembly 64 across the lens of the laparoscope.

The air processing or conveying assembly 100 can be variously sized, configured, and constructed. In the embodiment exemplified in FIGS. 35A and 35B, the air processing or conveying assembly 100 includes, self contained within the housing, a driven air moving component 102. In the illustrated embodiment, the driven air moving component 100 comprises a powered turbine or a powered blower or fan 102. The turbine, blower or fan 102 is powered to rotate and establishing a flow of air from the insufflated CO2 environment present in the operating cavity, through a lumen in the wall of the trocar 98, and into the second branch 48. Desirably, the turbine, blower, or fan 102 is sized and configured to deliver airflow through the deflector assembly 64 at a rate of at least 1.0 l/min.

The air processing or conveying assembly 100 can further include, self-contained within the housing in the path of airflow established by the turbine, blower, or fan 102, one or more elements 104 that trap smoke, particulates, aerosolized pathogens, odors, chemical toxins, and other undesired agents from a physiologic airflow. For example, the element 104 can include a filter media. The filter media can be sized and configured to beneficially remove, e.g., airborne particles, smoke, pathogens, and toxins from the airflow.

The filter media 104 can comprise, e.g., at least one layer of an ultra low particulate air (ULPA) filtration material and/or a high efficiency particular air (HEPA) filtration material to remove a high percentage (e.g., 99+%) of airborne particles from the airflow. Such filtration materials can comprise, e.g., an array of randomly arranged microfibers—e.g., ULPA grade hydrophobic glass, PTFE, or polypropylene microfibers—which are sized and configured to remove small sized pollutants and particles (e.g., as small as 0.1 micron (aerosolized) particles), by interception, impaction, and/or diffusion in association with the media.

The filter media 104 can comprise, in addition to the ULPA and/or HEPA filtration material, at least one layer of a material that absorbs smoke, odors and chemical toxins from the airflow. The layer can be formed by or incorporate, e.g., carbon or charcoal based material, or a diatomaceous earth material, or other odor removing or reducing agents.

The air processing or conveying assembly 100 can further include, self-contained within the housing in the flow path established by the turbine, blower, or fan 102, a dehumidifying unit 106 for removing adsorbing water vapor from the airflow. The dehumidifying unit 106 can be variously sized and configured. The dehumidifying unit 106 can comprise, e.g., one or more desiccant materials having a high affinity for adsorbing water vapor, such as silica gel. The desiccant material can be sized and configured in a "rotor" form, comprising alternate layers of flat and corrugated sheets impregnated with the active component (desiccant) to form a large number of axial air channels running parallel through the rotor structure. As air passes through these channels, moisture is transferred between the air and the desiccant.

Alternatively, the dehumidifying unit 106 can comprise an electronic dehumidifier, using, e.g., a peltier heat pump to generate a cool surface for condensing the water vapor from the airflow. Electronic dehumidifiers have the benefit of being very quiet when in use, and make possible very small dehumidifying units 106.

Desirably, the dehumidifying unit 106 provides a dehumidified airflow having a moisture content of 25 parts per million by volume or less.

The air processing or conveying assembly 100 desirably includes, self-contained within the housing, a source of power 108 for the driven turbine, blower or fan 102 and other components requiring energy to function, e.g., the electronic dehumidifying unit 106 (if present). The source of energy 108 may comprise, e.g., a battery which is rechargeable, or a disposable battery or batteries which are replaced, or a capacitor.

In the arrangement shown in FIG. 35A, the second branch 48 of the tubing set 16 delivers air processed by the air processing or conveying assembly 100 to the quick exchange coupler 22. When coupled to the manifold 18, the air processed by the air processing or conveying assembly 100 is continuously conveyed through lumens in the sheath 14 to a deflector assembly 64 at the distal end of the sheath 14. The deflector assembly 64 is sized and configured to direct the air processed by the air processing or conveying assembly 100 in a prescribed flow path and flow velocity continuously across the laparoscopic lens, in the manner previously described. The desired flow path and flow velocity of air processed by the air processing or conveying assembly 100 established by the deflector assembly 64 across the laparoscopic lens creates a continuous "wind shear," which in this embodiment is independent of operation of the insufflation circuit. The wind shear path of air processed by the air processing or conveying assembly 100 (being dehumidified) prevents laparoscopic lens fogging. The wind shear path or air processed by the air processing or conveying assembly 100 (being also treated to remove smoke and other debris) also desirably serves to deflect smoke and surgical debris away from the laparoscopic lens during surgery, in the manner previously described.

Figures 37, 38:
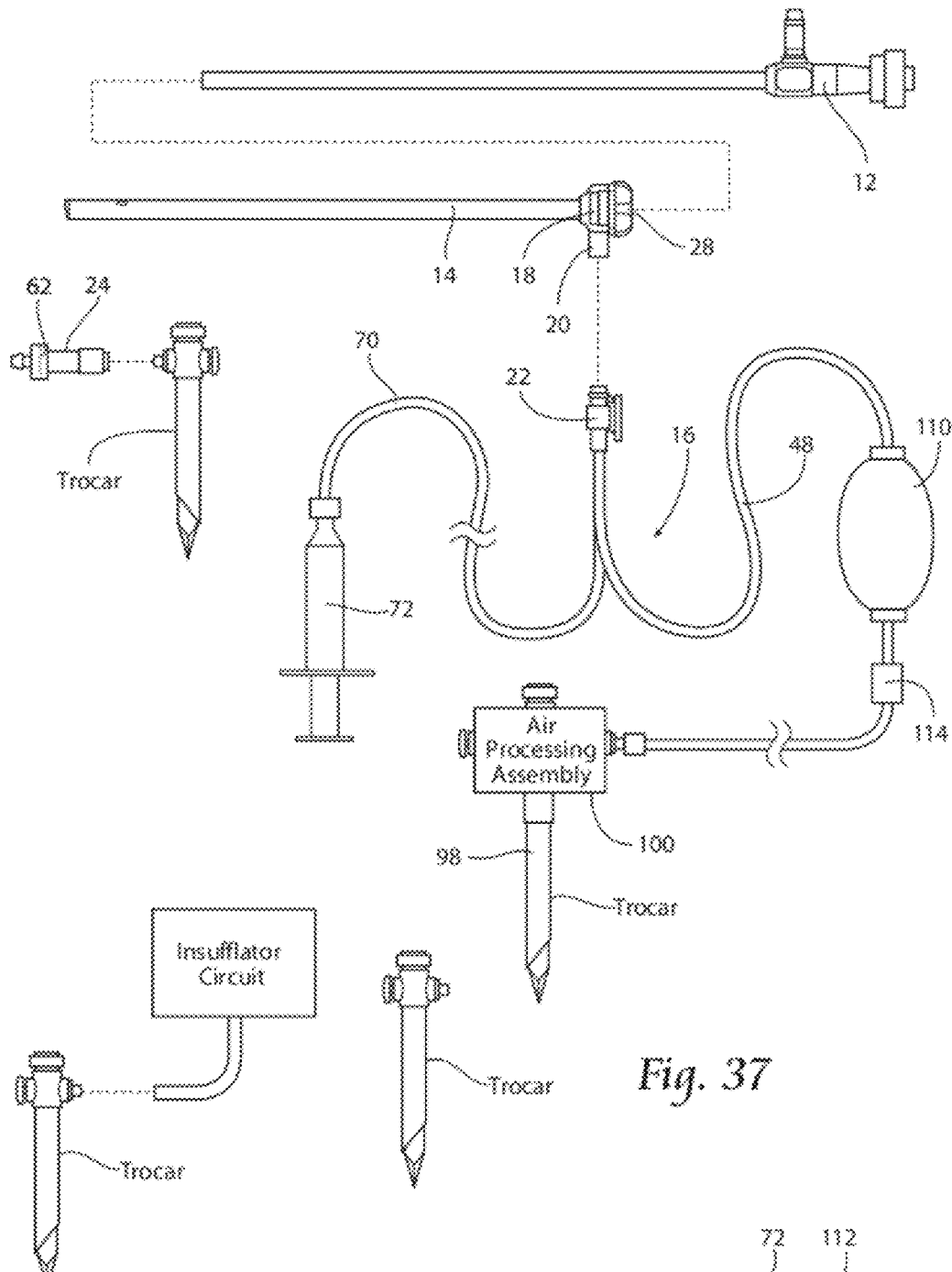
FIG. 37 shows a view optimizing assembly for use with a laparoscope having an air processing or conveying assembly that forms an integrated part of a trocar that is used in association with the assembly.
FIG. 38 shows a pump filled with sterile fluid with a "surface-active agent" or surfactant that can be operated in association with a view optimizing assembly like that shown in the preceding drawings.

As further shown in FIG. 35A, and as previously described, the assembly 10 can include a pump 72 (e.g., the 20 cc syringe) filled with sterile fluid (preferably with a "surface-active agent" or surfactant 112, as FIG. 38 further shows). As previously described, the pump 72 can be operated by personnel at the OR table to flush sterile fluid through the deflector assembly 64 of the sheath 14. The deflector assembly 64 directs the fluid bursts across the lens in a path generally 90-degress offset from the airflow path, as previously described.

In this arrangement, the tubing set 16 can also include an in-line bulb 110 carried in an upstream flow direction from the air processing or conveying assembly 100. The tubing set 16 also includes, in an upstream flow direction from the bulb 110, a one-way valve 114 that prevents fluid flow from the bulb 110 toward the air processing or conveying assembly 100. The bulb 110 can be pumped several times introduce bursts of air processed by the air processing or conveying assembly 100 through the deflector assembly 64, to clear liquid droplets off the lens and away from the deflector assembly 64, to maintain to the continuous directed flow of air processed by the air processing assembly 100 across the laparoscopic lens.

The air processing or conveying assembly 100 can be incorporated into a view optimizing assembly 10 in various other ways to provide a treated airflow continuously to the deflector assembly 64, independent of operation of an insufflation circuit.

Figure 36:
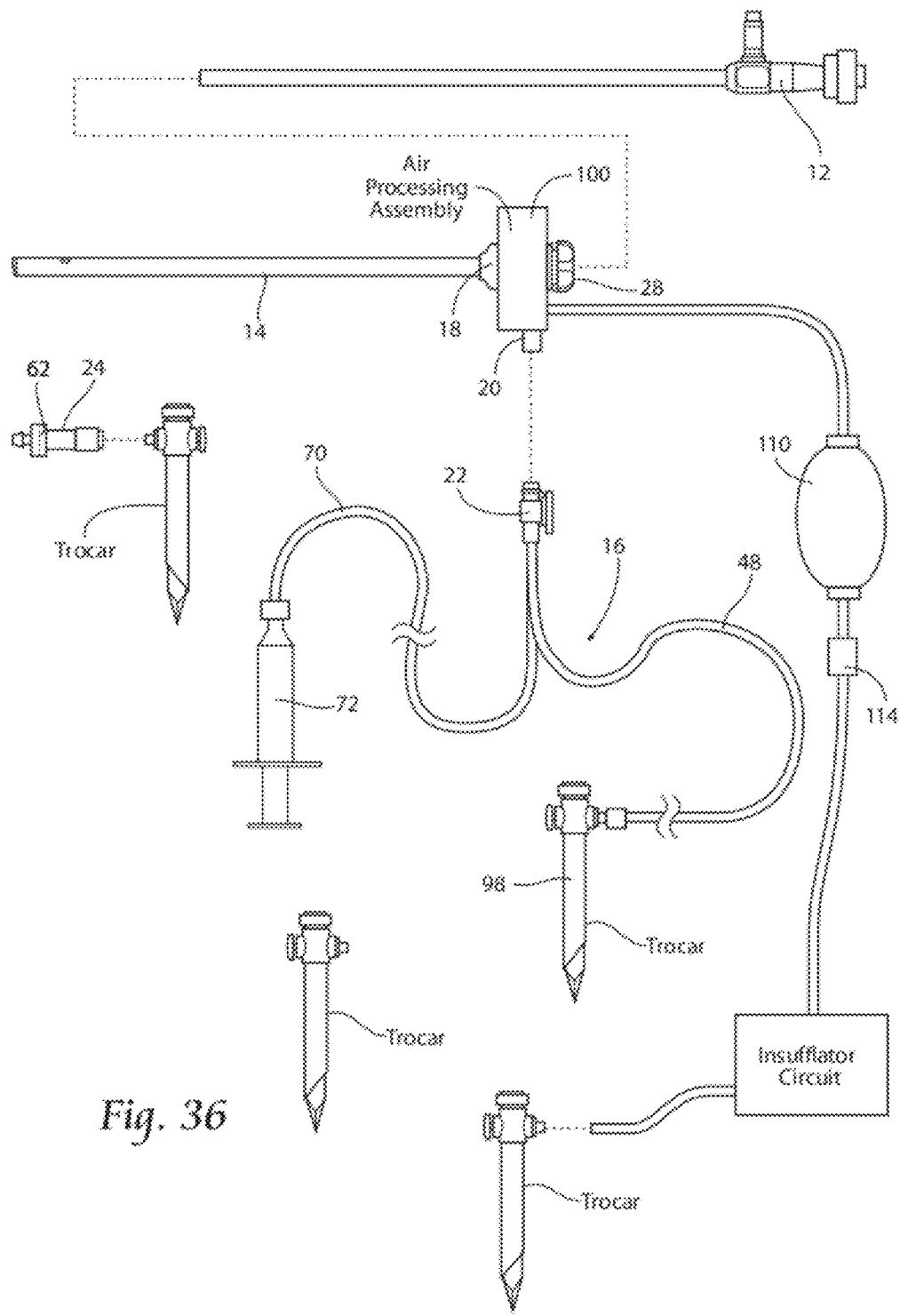
FIG. 36 shows a view optimizing assembly for use with a laparoscope having an air processing or conveying assembly that forms an integrated part of the sheath component of the assembly.

For example, as shown in FIG. 36, the air processing or conveying assembly 100 can be an integrated component of the sheath 14 itself. In this arrangement, the sheath-integrated air processing assembly 100 is supplied by air from the dedicated trocar 98 communicating with the insufflated $CO_2$ environment of the operating cavity, in the manner previously described. In this arrangement, the driven turbine, blower or fan 102, and optionally the filter media 104 and/or the dehumidifying unit 106 self-contained within the sheath-integrated air processing or conveying assembly 100, conduct and treat air drawn from the insufflated $CO_2$ environment of the operating cavity for direct conveyance in treated and dehumidified form continuously to the deflector assembly 64.

In this arrangement, as shown in FIG. 36, the in-line bulb 110 and one-way valve 114 assembly used to clear from the lens droplets of sterile fluid delivered by the pump 72, desirably communicates in parallel with the insufflation circuit, and not in-line with the air processing or conveying assembly 100. In this arrangement, the bulb 110 is squeezed to pump bursts of $CO_2$ from the insufflation circuit, when desired, to clear the liquid droplets off the lens and away from the deflector assembly 64.

In another illustrative embodiment, as shown in FIG. 37, the air processing or conveying assembly 100 can be an integrated component of the trocar 98 itself. In this arrangement, the driven turbine, blower, or fan 102, and optionally the filter media 104 and/or the dehumidifying unit 106 self-contained within the trocar-integrated air processing or conveying assembly 100, conduct and treat air from the trocar 98 for conveyance in treated and dehumidified form continuously to the deflector assembly 64. In this arrangement, as shown in FIG. 37, the in-line bulb 110 and one-way valve 114 assembly used to clear from the lens droplets of sterile fluid delivered by the pump 72 desirably communicates in-line with the trocar-integrated air processing or conveying assembly 100. In use, the bulb 110 is squeezed to pump bursts of air processed by the air processing assembly 100, when desired, to clear the liquid droplets off the lens and away from the deflector assembly 64.

The invention therefore makes possible an assembly comprising a self contained air conveying component coupled to a sheath that is sized and configured to receive a laparoscope including a laparoscopic lens providing visualization of an operating cavity. The air conveying component comprises an air flow path having an inlet sized and configured for communication with a source of $CO_2$ and an outlet. The air conveying component includes a driven air moving component in communication with the air flow path sized and configured to continuously convey $CO_2$ from the source through the air flow path to the outlet. The sheath coupled to the air conveying component can include a lumen communicating with the outlet of the air conveying mechanism for passing $CO_2$ continuously conveyed by the driven air coving component across the laparoscopic lens to maintain visualization of the operating cavity. The sheath and self-contained air conveying component can comprise an integrated assembly.

The invention also makes possible an assembly comprising a laparoscopic access device for accessing an operating cavity insufflated with $CO_2$ by operation of an insufflator circuit coupled to a self-contained air conveying component. The air conveying component comprises an air flow path having an inlet in fluid communication with operating cavity and an outlet sized and configured for fluid communication with an external instrument. The air conveying component includes an air moving component in communication with the air flow path. The air conveying component is sized and configured to be continuously driven independent of the insufflator circuit to convey $CO_2$ from the operating cavity continuously through the air flow path to the external instrument. The external instrument can itself comprise a sheath sized and configured to receive a laparoscope including a laparoscopic lens providing visualization of the operating. In this arrangement, the sheath includes a lumen communicating with the outlet of the air conveying component for passing $CO_2$ continuously conveyed by the driven air coving component across the laparoscopic lens to maintain visualization of the operating cavity.

Figure 39A:
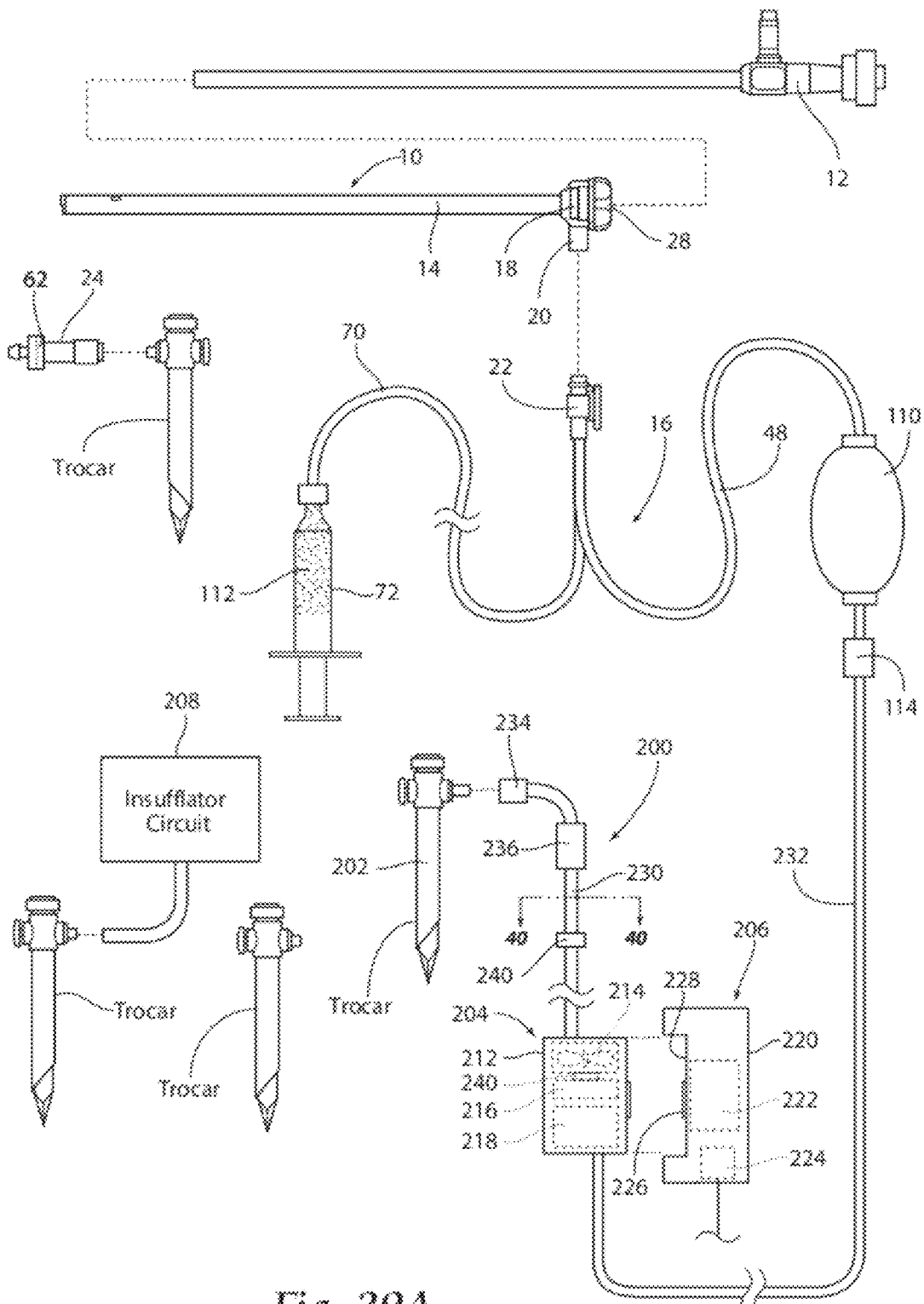
FIGS. 39A and 39B are, respectively, unassembled and assembled views of an exemplary embodiment of a closed loop air conditioning system for a view optimizing assembly, which includes a disposable air conditioning set and a durable air conditioning driver that can be coupled for use and uncoupled after use.

A further exemplary embodiment a closed loop air conditioning system 200 for a view optimizing assembly 10 (as previously described) that embodies features of the invention is shown in FIG. 39A. In FIG. 39A, the system 200 includes three principal components. These are (i) an air source access device 202 (also called a trocar), which is sized and configured to placed through an incision and provides communication with an insufflated CO2 environment in an operating cavity (which is independently supplied by an insufflation circuit 208 through another trocar, as FIG. 39A shows); (ii) an air conditioning set 204, which is sized and configured to couple to the an air source access device 202 and the manifold 18 of the view optimizing assembly 10; and (iii) an air conditioning driver 206 that interacts with the air conditioning set 204 to convey air through from the air source access device 202 to the view optimizing assembly 10.

The air conditioning driver 206 is intended to be a durable item capable of long term, maintenance free use. The air conditioning driver 206 also desirably presents a compact footprint, suited for operation upon a table top or other relatively small surface normally found in the OR (see FIG. 39B).

Figures 39B, 40:
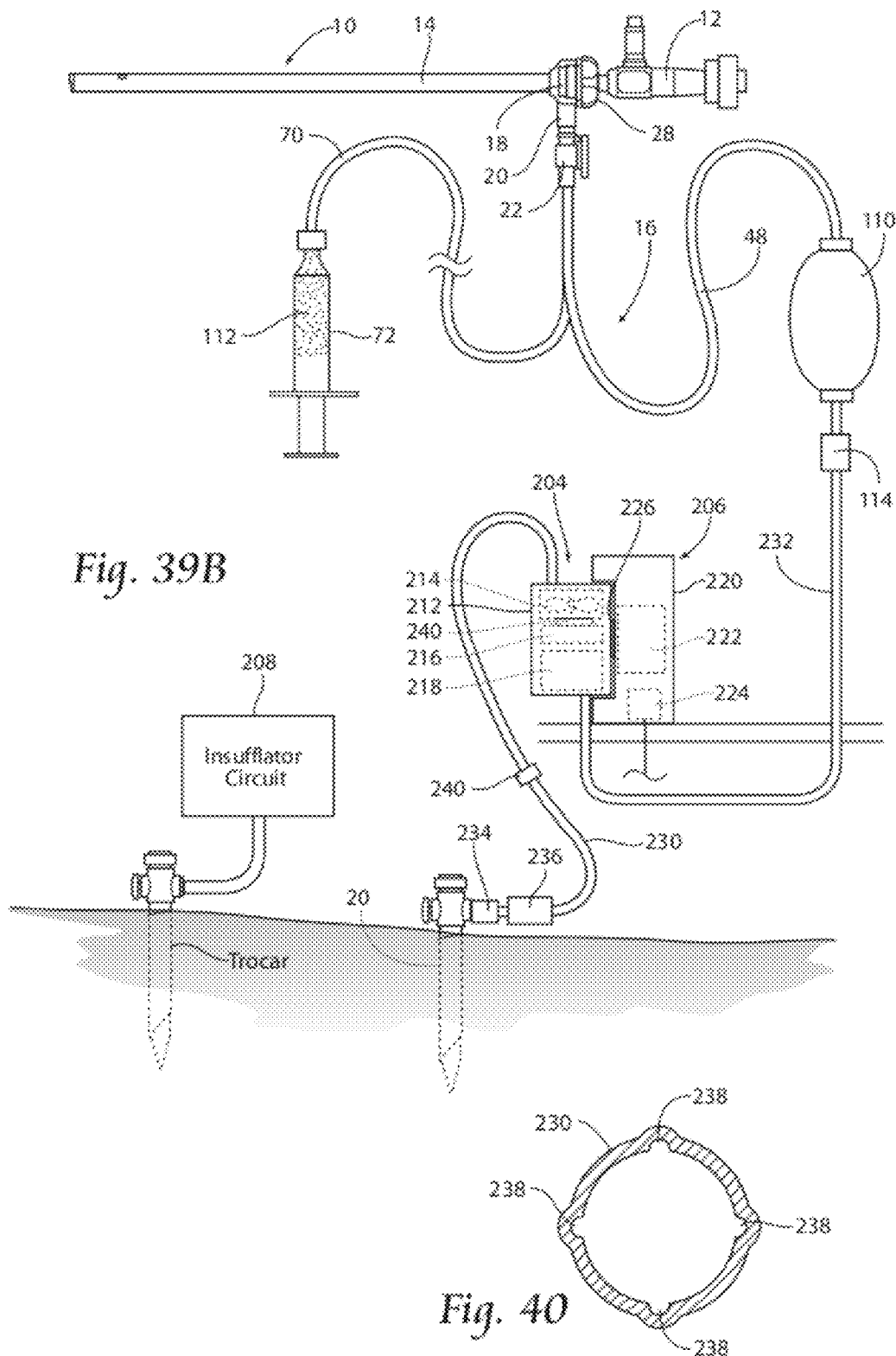
FIG. 40 is a section view of an exemplary arrangement of moisture drain channels formed along the interior wall of flow inlet tubing that the closed loop air conditioning system shown in FIGS. 39A and 39B can incorporate, if desired, taken generally along line 40-40 of FIG. 39A.

Like the view optimizing assembly 10, the air source access device 202 and the air conditioning set 204 are intended to be a single use, disposable items. As shown in FIG. 39B, after coupling the insufflation circuit 208 to the operating cavity at the outset if a surgical procedure, the operating team places the air source access device 202 through an incision, as they would a conventional trocar. As FIG. 39B shows, the operating team couples the air conditioning set 204 to the air source access device 202 as well as to the view optimizing assembly 10. The operating team loads the air conditioning set 204 onto the air conditioning driver 206. Upon the completing the surgical procedure, the surgical team unloads the air conditioning set 204 from the air conditioning driver 206 and discards it, along with the view optimizing assembly 10 and the air source access device 202.

When coupled to the air conditioning driver 206, components of the air conditioning set 204 serve to draw air from the insufflated CO2 environment present in the operating cavity through the air source access device 202, for delivery by the view optimizing assembly 10 continuously across the lens of the laparoscope, independent of operation of the insufflation circuit 208 itself. Even as the insufflation circuit 208 intermittently cycles on and off, the closed loop air conditioning system 200 operates to continuously draw air from the insufflated CO2 environment present in the operating cavity, for continuous conveyance to the view optimizing assembly 10.

Operating independent of the insufflation circuit 208, the pressure of air delivered by closed loop air conditioning system 200 is not only continuous, but it is also not constrained by the limits imposed upon the insufflation pressure (which is typically about a maximum of 15 mmHg). The pressure of air delivered by closed loop air conditioning system 200 can be selectively adjusted higher than the maximum insufflation pressure to further optimize the beneficial functions provided by the view optimizing assembly 10, as has been previously described. For example, the pressure of air delivered to the view optimizing assembly 10 by the air conditioning system 200 can be increased, if desired, e.g., within a range of between 1 PSI and 5 PSI, to provide enhanced defogging and debris removal by the view optimizing assembly 10. Further, the closed loop air conditioning system 200 can also serve to beneficially process or treat the air drawn from the insufflated CO2 environment present in the operating cavity, after it is removed from the operating cavity and before it is conducted to the view optimizing assembly 10, to remove, e.g., smoke, particulates, aerosolized pathogens, and water vapor from the airflow before it is conducted by the view optimizing assembly 10 across the lens of the laparoscope.

The air conditioning set 204 can be variously constructed. In an exemplary arrangement (see FIGS. 39A and 39B), the air conditioning set 204 includes a canister 212 that houses in a series flow relationship, e.g., a driven air moving component 214; one or more elements 216 that trap smoke, particulates, aerosolized pathogens, odors, chemical toxins, and other undesired agents from a physiologic airflow; and dehumidifying unit 218 for removing or adsorbing water vapor from the airflow.

Examples of such components have already been described in the context of other exemplary embodiments.

As previously described, the driven air moving component 214 can comprise, e.g., a powered turbine or a powered blower or fan. Desirably, the turbine, blower, or fan is sized and configured to deliver airflow at a rate of at least 1.0 l/min.

As previously described, the elements 216 can include, e.g., a filter media (including, e.g., at least one layer of an ultra low particulate air (ULPA) filtration material and/or a high efficiency particular air (HEPA) filtration material to remove a high percentage (e.g., 99+%) of airborne particles from the airflow, and at least one layer of a material that absorbs smoke, odors and chemical toxins from the airflow, such as a carbon or charcoal based material, or a diatomaceous earth material, or other odor removing or reducing agents.

As before described, the dehumidifying unit 218 can comprise, e.g., one or more desiccant materials having a high affinity for adsorbing water vapor, such as silica gel or an electronic dehumidifier, using, e.g., a peltier heat pump to generate a cool surface for condensing the water vapor from the airflow. Desirably, the dehumidifying unit 218 provides a dehumidified airflow having a moisture content of 25 parts per million by volume or less.

The air conditioning driver 206 desirably includes, self-contained within a housing 220, a driver 222 and source of power 224 for the driven turbine, blower or fan and other components within the canister 212 requiring energy to function, e.g., the electronic dehumidifying unit (if present).

The air conditioning driver 222 can be various constructed. The driver 222 can include a drive motor that selectively couples and decouples to the driven turbine, blower or fan, e.g., by a mechanically interlocking or a magnetic coupling 226. The source of power 224 may also comprise, e.g., an interior battery for the motor, or a plug for connecting the motor to an external electrical source.

The housing 220 can include, e.g., a canister docking station 228. Inserting the canister 212 into the docking station 228 couples the driven turbine, blower or fan to the motor, as well as couples power to the other components within the canister 212 requiring energy to function. Removing the canister 212 from the docking station 228 decouples the components of the canister 212, allowing their disposal as a unit.

The air conditioning set 204 can also include flexible flow inlet tubing 230 and flexible flow outlet tubing 232 integrally coupled to the canister 212, or individually coupled by leur connectors at the instance of use. The flexible flow inlet tubing 230 and flexible flow outlet tubing 232 can comprise individual lengths of medical grade tubing, or take the form of extruded dual lumen tubing.

The flexible flow inlet tubing 230 desirably includes a conventional luer connector 234 at its proximal end to couple to a stop cock/leur fitting on the air source access device 202.

At or near its proximal end, the flexible flow inlet tubing 230 also desirably includes a moisture trap 236 or a functionally equivalent structure to separate moisture as it condenses in the OR from the hotter humid air drawn from the operating cavity. It is desirable to accommodate the presence of condensing moisture as soon as possible after its withdrawal from the cavity and entry into the cooler OR environment, well prior to its conveyance into the canister 212, where further dehumidification and conditioning can occur. Separately, or in combination (see FIG. 40), the interior walls of the flexible flow inlet tubing 230 can include formed interior drain channels 238 to facilitate run-off of moisture and mitigate against the collection of water in a gravity-low (trap) position created during use of the flexible flow inlet tubing 230.

The flexible flow outlet tubing 232 desirably includes at its distal end a quick exchange coupler 22, as previously described. When the flexible flow outlet tubing 232 is coupled to the manifold 18 of the view optimizing assembly 10, the view optimizing assembly 10 continuously conveys the air conditioned by the components of the canister 212 in a prescribed flow path and flow velocity across the laparoscopic lens, in the manner previously described, independent of operation of the insufflations circuit 218. The conditioned air prevents laparoscopic lens fogging, as well as also desirably serves to deflect smoke and surgical debris away from the laparoscopic lens during surgery, in the manner previously described.

As further shown in FIGS. 39A and 39B, and as previously described, the flexible flow outlet tubing 222 can also include a pump 72 (e.g., the 20 cc syringe) filled with sterile fluid (preferably with a "surface-active agent" or surfactant 112, as FIG. 38 also shows). As previously described, the pump 72 can be operated by personnel at the OR table to flush sterile fluid across the lens, as previously described.

In this arrangement, and as further shown in FIGS. 39A and 39B, the flexible flow outlet tubing 232 can also include an in-line bulb 110 carried in an upstream flow direction from the canister 212, along with a one-way valve 114 that prevents fluid flow from the bulb 110 toward the canister 212. The bulb 110 can be pumped several times to introduce bursts of air processed by the canister 212 across the lens, to clear liquid droplets off the lens, as previously described.

The flexible flow inlet tubing 230 and the flexible flow outlet tubing 232 can also carry one or more sensing elements 240. One or more sensing elements 240 can also be located within the canister. The sensing elements 240 can monitor, e.g., (i) airflow velocity and/or pressure in the flexible flow inlet tubing 230 and/or flexible flow outlet tubing 232 and/or canister 212; (ii) mean absolute humidity levels in the flexible flow inlet tubing 230 and/or flexible flow outlet tubing 232 and/or canister 212; (iii) temperature in the flexible flow inlet tubing 230 and/or flexible flow outlet tubing 232 and/or canister 212; (iv) density of smoke, particulates, aerosolized pathogens, chemical toxins, and other undesired agents in the flexible flow inlet tubing 230 and/or flexible flow outlet tubing 232 and/or canister 212; (v) odors in the flexible flow inlet tubing 230 and/or flexible flow outlet tubing 232 and/or canister 212; (vi) mechanical malfunction of the driven turbine, blower or fan and/or other components within the canister 212; and (vii) other prescribed conditions in the flexible flow inlet tubing 230 and/or flexible flow outlet tubing 232 and/or canister 212. The sensing elements 240 can be coupled to a processor in the canister 212 and conditioned to call for a termination of operation of the system 200, should predetermined out of bound conditions be sensed.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A surgical system for use with an insufflator circuit, the surgical system comprising:
   a sheath sized and configured to receive a laparoscope;
   an air source access device sized and configured to provide communication with an insufflated operating cavity,
   an air conditioning set sized and configured to couple to the air source access device and the sheath, the air conditioning set including a powered air moving fan; and
   an air conditioning driver configured to be selectively attached and detached from the air conditioning set during normal use, the air conditioning driver including a source of power and a drive motor therein to drive the powered air moving fan so as to convey air from the insufflated operating cavity through the air source access device, through the air conditioning set, and through the sheath for passage across a lens of the laparoscope, to thereby maintain visualization of the insufflated operating cavity independent of operation of the insufflator circuit.

2. A system according to claim 1 wherein the air conditioning set is disposable.

3. A system according to claim 1 wherein the air conditioning set includes an air treatment component configured to remove at least one undesired agent.

4. A system according to claim 3 wherein the undesired agent comprises one or more of smoke, particulates, pathogens, odors, and toxins.

5. A system according to claim 3 wherein the air treatment component comprises a filter media.

6. A system according to claim 5 wherein the filter media includes an ultra low particulate air filtration media.

7. A system according to claim 5 wherein the filter media includes a high efficient particulate air filtration media.

8. A system according to claim 5 wherein the filter media includes a material that absorbs at least one of smoke, odors, and toxins.

9. A system according to claim 1 wherein the air conditioning set includes a moisture removing element.

10. A system according to claim 1 wherein the air conditioning set includes inlet tubing sized and configured to couple with the air source access device and outlet tubing sized and configured to couple with the lumen of the sheath.

11. A system according to claim 10 wherein at least one of the inlet and outlet tubing includes a moisture trap.

12. A system according to claim 10 wherein the inlet tubing includes a moisture trap adjacent to the air source access device.

13. The system of claim 1, wherein the powered air moving fan is configured to deliver airflow at a rate of at least 1.0 L/min.

14. The system of claim 1, wherein the air conditioning driver is reusable.

* * * * *